(12) United States Patent
Gilbert et al.

(10) Patent No.: US 8,435,309 B2
(45) Date of Patent: May 7, 2013

(54) JOINT ACTUATION MECHANISM FOR A PROSTHETIC AND/OR ORTHOTIC DEVICE HAVING A COMPLIANT TRANSMISSION

(75) Inventors: Benoit Gilbert, Lac Beauport (CA); David Landry, Saint-Chrysostome (CA)

(73) Assignee: Victhom Human Bionics, Saint-Augustin-de-Desmaures (CA)

( * ) Notice: Subject to any disclaimer, the term of this patent is extended or adjusted under 35 U.S.C. 154(b) by 72 days.

(21) Appl. No.: 12/160,727

(22) PCT Filed: Jan. 7, 2008

(86) PCT No.: PCT/CA2008/000011
§ 371 (c)(1),
(2), (4) Date: Jul. 7, 2009

(87) PCT Pub. No.: WO2008/080231
PCT Pub. Date: Jul. 10, 2008

(65) Prior Publication Data
US 2009/0299480 A1 Dec. 3, 2009

Related U.S. Application Data

(60) Provisional application No. 60/878,689, filed on Jan. 5, 2007.

(51) Int. Cl.
*A61F 2/70* (2006.01)
*A61F 2/64* (2006.01)
(52) U.S. Cl.
USPC .............................................. 623/39; 623/24
(58) Field of Classification Search .............. 623/39–46, 623/24–26
See application file for complete search history.

(56) References Cited

U.S. PATENT DOCUMENTS

| 4,030,141 A | 6/1977 | Graupe |
| 4,179,759 A | 12/1979 | Smith |

(Continued)

FOREIGN PATENT DOCUMENTS

| CA | 2546858 A1 | 6/2005 |
| CN | 2400072 Y | 10/2000 |

(Continued)

OTHER PUBLICATIONS

Flowers et al., Journal of Biomedical Engineering: Transactions of the ASME; Feb. 1977, pp. 3-8.

(Continued)

*Primary Examiner* — David Isabella
*Assistant Examiner* — Marcia Hoffman
(74) *Attorney, Agent, or Firm* — Knobbe Martens Olson & Bear LLP

(57) ABSTRACT

Disclosed herein a prosthetic or orthotic device having a joint portion and a compliant transmission assembly in operational communication with the joint portion. The device restores the normal capabilities and natural dynamics of a healthy joint for common activities. The compliant transmission assembly includes a compliant element. The compliant transmission assembly absorbs energy when a torque is applied between a prosthetic or orthotic device portion and another adjacent device portion or the adjacent limb segment of the user. The compliant element of the invention absorbs energy during flexion of a joint for the dampening thereof and releases this energy during extension of the joint for assistance thereof. Also disclosed herein is an actuator assembly, a torque sensor and an actuator locking device as well as a method for determining the torque of such prosthetic and orthotic devices.

43 Claims, 17 Drawing Sheets

U.S. PATENT DOCUMENTS

| | | |
|---|---|---|
| 4,518,307 A | 5/1985 | Bloch |
| 4,521,924 A | 6/1985 | Jacobsen et al. |
| 4,558,704 A | 12/1985 | Petrofsky |
| 4,600,357 A | 7/1986 | Coules |
| 4,617,920 A | 10/1986 | Carsalade |
| 4,657,470 A | 4/1987 | Clarke et al. |
| 4,776,852 A | 10/1988 | Rubic |
| 4,843,921 A | 7/1989 | Kremer |
| 4,865,024 A | 9/1989 | Hensley et al. |
| 4,872,803 A | 10/1989 | Asakawa |
| 4,989,161 A | 1/1991 | Oaki |
| 4,994,086 A | 2/1991 | Edwards |
| 5,012,591 A | 5/1991 | Asakawa |
| 5,062,856 A | 11/1991 | Sawamura et al. |
| 5,062,857 A | 11/1991 | Berringer |
| 5,133,773 A | 7/1992 | Sawamura et al. |
| 5,133,774 A | 7/1992 | Sawamura et al. |
| 5,174,168 A | 12/1992 | Takagi et al. |
| 5,201,772 A | 4/1993 | Maxwell |
| 5,246,465 A | 9/1993 | Rincoe et al. |
| 5,252,102 A | 10/1993 | Singer et al. |
| 5,327,790 A | 7/1994 | Levin et al. |
| 5,376,133 A | 12/1994 | Gramnas |
| 5,383,939 A | 1/1995 | James |
| 5,394,132 A | 2/1995 | Poil |
| 5,443,528 A | 8/1995 | Allen |
| 5,476,441 A | 12/1995 | Durfee et al. |
| 5,571,205 A | 11/1996 | James |
| 5,571,213 A | 11/1996 | Allen |
| 5,650,704 A | 7/1997 | Pratt et al. |
| 5,704,946 A | 1/1998 | Greene |
| 5,746,774 A | 5/1998 | Kramer et al. |
| 5,779,735 A | 7/1998 | Molino |
| 5,800,561 A | 9/1998 | Rodriguez |
| 5,888,212 A | 3/1999 | Petrofsky et al. |
| 5,888,213 A | 3/1999 | Sears et al. |
| 5,888,246 A | 3/1999 | Gow |
| 5,893,891 A | 4/1999 | Zahedi |
| 5,895,430 A | 4/1999 | O'Connor |
| 6,007,582 A | 12/1999 | May |
| 6,113,642 A | 9/2000 | Petrofsky et al. |
| 6,206,932 B1 | 3/2001 | Johnson |
| 6,206,933 B1 | 3/2001 | Shorter et al. |
| 6,361,570 B1 | 3/2002 | Gow |
| 6,425,925 B1 | 7/2002 | Grundei |
| 6,443,993 B1 | 9/2002 | Koniuk |
| 6,494,039 B2 | 12/2002 | Pratt et al. |
| 6,517,585 B1 | 2/2003 | Zahedi et al. |
| 6,517,858 B1 | 2/2003 | Le Moel et al. |
| 6,610,101 B2 | 8/2003 | Herr et al. |
| 6,613,097 B1 | 9/2003 | Cooper |
| 6,645,252 B2 | 11/2003 | Asai et al. |
| 6,708,103 B2 | 3/2004 | Herr et al. |
| 6,755,870 B1 | 6/2004 | Biedermann et al. |
| 6,761,743 B1 | 7/2004 | Johnson |
| 6,908,488 B2 | 6/2005 | Passivaara |
| 7,029,500 B2 | 4/2006 | Martin |
| 7,066,896 B1 | 6/2006 | Kiselik |
| 7,131,998 B2 | 11/2006 | Pasolini |
| 7,137,998 B2 | 11/2006 | Bedard et al. |
| 7,147,667 B2 | 12/2006 | Bedard |
| 7,279,009 B2 | 10/2007 | Herr et al. |
| 7,295,892 B2 | 11/2007 | Herr et al. |
| 7,314,490 B2 | 1/2008 | Bedard et al. |
| 7,393,364 B2 | 7/2008 | Martin |
| 7,396,337 B2 | 7/2008 | McBean et al. |
| 7,552,664 B2 * | 6/2009 | Bulatowicz ............... 74/640 |
| 7,588,604 B2 | 9/2009 | Okuda et al. |
| 7,637,957 B2 | 12/2009 | Ragnarsdóttir et al. |
| 7,637,959 B2 | 12/2009 | Clausen et al. |
| 7,655,050 B2 | 2/2010 | Palmer et al. |
| 7,704,283 B2 | 4/2010 | Ninomiya |
| 7,731,759 B2 | 6/2010 | Pusch et al. |
| 7,736,394 B2 | 6/2010 | Bedard et al. |
| 7,799,091 B2 | 9/2010 | Herr et al. |
| 7,815,689 B2 | 10/2010 | Bedard et al. |
| 7,867,284 B2 | 1/2011 | Bedard |
| 7,992,849 B2 | 8/2011 | Sugar et al. |
| 8,075,633 B2 | 12/2011 | Herr et al. |
| 2001/0029400 A1 | 10/2001 | Deffenbaugh et al. |
| 2002/0052663 A1 | 5/2002 | Herr et al. |
| 2002/0198604 A1 | 12/2002 | Schulman et al. |
| 2004/0039454 A1* | 2/2004 | Herr et al. .............. 623/39 |
| 2004/0064195 A1 | 4/2004 | Herr |
| 2004/0181289 A1* | 9/2004 | Bedard et al. .......... 623/24 |
| 2004/0193286 A1 | 9/2004 | Grundai |
| 2005/0107889 A1 | 5/2005 | Bedard et al. |
| 2006/0085082 A1* | 4/2006 | Asgeirsson et al. ........ 623/26 |
| 2006/0122710 A1 | 6/2006 | Bedard |
| 2006/0122711 A1 | 6/2006 | Bedard et al. |
| 2006/0201757 A1 | 9/2006 | Dupuis et al. |
| 2006/0206043 A1 | 9/2006 | Yakimovich et al. |
| 2006/0249315 A1 | 11/2006 | Herr et al. |
| 2006/0259153 A1* | 11/2006 | Harn et al. .............. 623/44 |
| 2007/0016329 A1 | 1/2007 | Herr et al. |
| 2007/0043449 A1 | 2/2007 | Herr et al. |
| 2007/0083272 A1 | 4/2007 | Van De Veen |
| 2007/0123997 A1 | 5/2007 | Herr et al. |
| 2007/0162152 A1 | 7/2007 | Herr et al. |
| 2008/0046096 A1 | 2/2008 | Bedard et al. |
| 2008/0058959 A1 | 3/2008 | Bedard et al. |
| 2008/0097269 A1* | 4/2008 | Weinberg et al. ........... 602/16 |
| 2009/0054996 A1 | 2/2009 | Sykes |
| 2010/0262260 A1 | 10/2010 | Bedard et al. |
| 2010/0305716 A1 | 12/2010 | Pusch et al. |
| 2010/0324699 A1 | 12/2010 | Herr et al. |
| 2011/0087339 A1 | 4/2011 | Pusch et al. |
| 2011/0130847 A1 | 6/2011 | Bedard et al. |
| 2011/0137429 A1 | 6/2011 | Bedard |
| 2011/0257764 A1 | 10/2011 | Herr et al. |
| 2012/0191220 A1 | 7/2012 | Bedard et al. |
| 2012/0191221 A1 | 7/2012 | Bedard et al. |

FOREIGN PATENT DOCUMENTS

| | | |
|---|---|---|
| DE | 4229330 A1 | 3/1994 |
| DE | 19859931 | 7/2000 |
| EP | 0549855 A2 | 7/1993 |
| EP | 1166726 A1 | 1/2002 |
| EP | 1169982 A1 | 1/2002 |
| FR | 2293185 | 7/1976 |
| FR | 2623086 | 5/1989 |
| GB | 2201260 | 8/1988 |
| GB | 2 260 495 | 4/1993 |
| GB | 2 302 949 A | 2/1997 |
| JP | 59-32453 | 2/1984 |
| JP | 01-244748 A | 9/1989 |
| JP | 5-161668 | 6/1993 |
| JP | 11056885 | 3/1999 |
| JP | 11-215793 | 8/1999 |
| JP | 2002-191654 A | 7/2002 |
| JP | 2002-219141 | 8/2002 |
| JP | 2005-500 A | 1/2005 |
| KR | 10-2006-0105026 | 10/2006 |
| WO | WO 94/09727 A2 | 5/1994 |
| WO | WO96/41599 | 12/1996 |
| WO | WO 97/27822 | 8/1997 |
| WO | WO99/08621 | 2/1999 |
| WO | WO00/30572 | 6/2000 |
| WO | WO00/38599 | 7/2000 |
| WO | WO01/54630 | 8/2001 |
| WO | WO 01/72245 | 10/2001 |
| WO | WO2005/051248 | 6/2005 |
| WO | WO2005/087144 | 9/2005 |

OTHER PUBLICATIONS

Aminian, K., Estimation of Speed and Incline of Walking Using Neural Network, IEEE Transactions on Instrumentation and Measurement 44(3):743-747, Jun. 1995.

Andrews, B.J., et al., Hybrid FES Orthosis Incorporating Closed Loop Control and Sensory Feedback, J. Biomed. Eng. 10:189-195, Apr. 1988.

Bar., A., et al., Adaptive Microcomputer Control of an Artificial Knee in Level Walking, J. Biomech. Eng. 5:145-150, 1983.

Bedard, S., et al., Actuated Leg Prosthesis for Above-Knee Amputees, U.S. Appl. No. 13/540,342, filed Jul. 2, 2012.

Blaya, J.A., Force-Controllable Ankle Foot Orthosis (AFO) to Assist Drop Foot Gait, Thesis, Massachusetts Institute of Technology, Jul. 8, 2003.

Dai, R., et al., Application of Tilt Sensors in Functional Electrical Stimulation, IEEE Tras. Rehab. Eng. 4(2):63-71, 1996.

Foerster, et al., Detection of Posture and Motion by Accelerometry: A Validation Study in Ambulatory Monitoring, Computers in Human Behavior 15:571-583, 1999.

Frank, K., Reliable Real-Time Recognition of Motion Related Human Activities Using MEMS Inertial Sensors, presented at the ION GNSS 2010, Sep. 24, 2010.

Hanafusa, et al., "A Robot Hand With Elastic Fingers and Its Application to Assembly Process," Robot Motion, Brady et al., MIT Press, 1982, pp. 337-359, Cambridge, MA.

Hayes, W.C., et al., Leg Motion Analysis During Gait by Multiaxial Accelerometry: Theoretical Foundations and Preliminary Validations, J. Biomech. Eng. 105:283-289, Aug. 1983.

Heyn, A., et al., The Kinematics of the Swing Phase Obtained From Accelerometer and Gyroscope Measurements, 18th Annual International Conference of the IEEE Engineering in Medicine and Biology Society, Amsterdam, 1996, pp. 463-464.

Howard, R.D., Joint and Actuator Design for Enhanced Stability in Robotic Force Control, Massachusetts Institute of Technology, Dept. of Aeronautics and Astronautics, Ph.D. Thesis, 1990.

Jonic, S., et al., Three Machine Learning Techniques for Automatic Determination of Rules to Control Locomotion, IEEE Transactions on Biomedical Engineering 46(3):300-310, 1999.

Kirkwood, C.A., et al., Automatic Detection of Gait Events: A Case Study Using Inductive Learning Techniques, J. Biomed. Eng. 11:511-516, 1989.

Kostov, A., et al., Machine Learning in Control of Functional Electrical Stimulation Systems for Locomotion, IEEE Transactions on Biomedical Engineering 42(6):543-553, 1995.

Lee, S., Activity and Location Recognition Using Wearable Sensors, Pervasive Computing, 2002, pp. 24-32.

Martin, C.W., Otto Bock C-leg: A Review of Its Effectiveness, WCB Evidence Based Group, Nov. 27, 2003.

Martin, J., Electronically Controlled Magnetorheological Fluid Prosthetic Foot, U.S. Appl. No. 60/371,974, filed Apr. 12, 2002.

Mayagoitia, R.E., et al., Accelerometer and Rate Gyroscope Measurement of Kinematics: An Inexpensive Alternative to Optical Motion Analysis Systems, J. Biomech. 35:537-542, 2002.

Moe-Nilssen, R., A New Method for Evaluating Motor Control in Gait Under Real-Life Environmental Conditions, Part 1—The Instrument, Clinical Biomechanics 13:320-327, 1998.

Moe-Nilssen, R., A New Method for Evaluating Motor Control in Gait Under Real-Life Environmental Conditions, Part 2: Gait Analysis, Clinical Biomechanics 13:328-335, 1998.

Nakagawa, A., Intelligent Knee Mechanism and the Possibility to Apply the Principle to the Other Joints, Proceedings of the 20th Annual International Conference of the IEEE Engineering in Medicine and Biology Society 20(5):2282, Dec. 1998.

Petrofsky, J.S., et al., Feedback Control System for Walking in Man, Comput. Biol. Med. 14(2):135-149, 1984.

Pfeffer, et al., Experiments with a Dual-Armed, Cooperative, Flexible-Drivetrain Robot System, Proceedings of the 1993 IEEE International Conference on Robotics & Automation, May 5, 1993, vol. 3, pp. 601-608.

Popovic, D., et al., Control Aspects of Active Above-Knee Prosthesis, Int. J. Man-Machine Studies 35(6):751, Dec. 1991.

Rapport de Recherche Europeenne issued in connection with EP 01169982, Nov. 6, 2001.

Reitman, J.S., et al., Gait Analysis in Prosthetics: Opinions, Ideas and Conclusions, Prosthetics and Orthotics International, 26:50-57, 2002.

Robinson, D.W., Design and Analysis of Series Elasticity in Closed-Loop Actuator Force Control, Doctoral Dissertation, Massachusetts Institute of Technology, Jun. 2000.

Sekine, M., et al., Classification of Waist-Acceleration Signals in a Continuous Walking Record, medical Engineering & Physics 22:285-291, 2000.

Smidt, G.L., et al., An Automated Accelerometry System for Gait Analysis, J. Biomech. 10:367-375, 1977.

Sugano, et al., Force Control of the Robot Finger Joint Equipped With Mechanical Compliance Adjuster, Proceedings of the 1992 IEEE/RSJ International Conference on Intelligent Robots & Systems, Jul. 1992, pp. 2005-2013.

Tomovic, R., et al., A Finite State Approach to the Synthesis of Bioengineering Control Systems, IEEE Transactions of Human Factors in Electronics HFE-7(2):65-69, Jun. 1966.

Tong, K., and M.H. Granat, A Practical Gait Analysis System Using Gyroscopes, Med. Eng. Phys. 21(2):87-94, Mar. 1999.

Tong, K.Y., et al., Virtual Artificial Sensor Technique for Functional Electrical Stimulation, Medical Engineering & Physics 20:458-468, 1998.

Van Der Kooij, H., et al., A Multisensory Integration Model of Human Stance Control, Biol. Cybern. 80:299-308, 1998.

Veltink, P.H., et al., Detection of Static and Dynamic Activities using Uniaxial Accelerometers, IEEE Transactions on Rehabilitation Engineering 4(4):375-385, 1996.

Veltink, P.H., et al., The Feasibility of Posture and Movement Detection by Accelerometry, 15th Annual International Conference of the IEEE Engineering in Medicine and Biology Society, Oct. 28-31, 1993, San Diego, California, pp. 1230-1231.

Willemsen, A. Th.M., et al., Real-Time Gait Assessment Utilizing a New Way of Accelerometry, J. Biomech. 23(8):859-863, 1990.

Williamson, M.M., Series Elastic Actuators, Master's Thesis, Massachusetts Institute of Technology, Artificial Intelligence Laboratory, A.I. Technical Report No. 1524, Jan. 1995.

Woodward, M.I., et al., Skeletal Accelerations Measured During Different Exercises, Proceedings of the Institution of Mechanical Engineers, Part H, J. Engin. Med. 207:79, 1993.

* cited by examiner

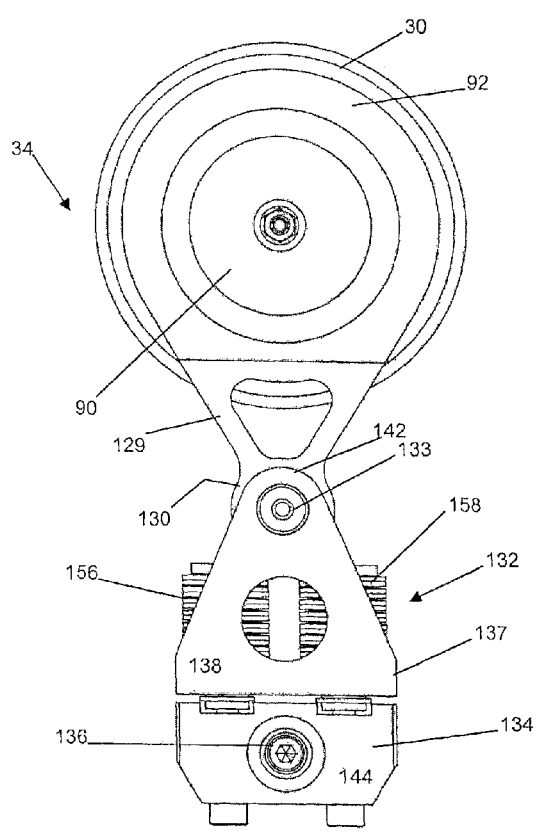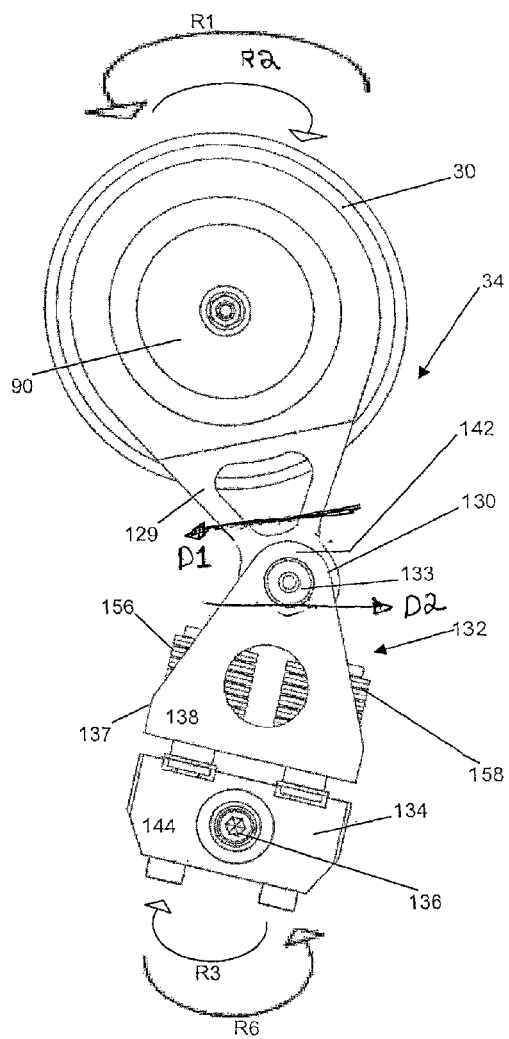
FIGURE 6
FIGURE 7

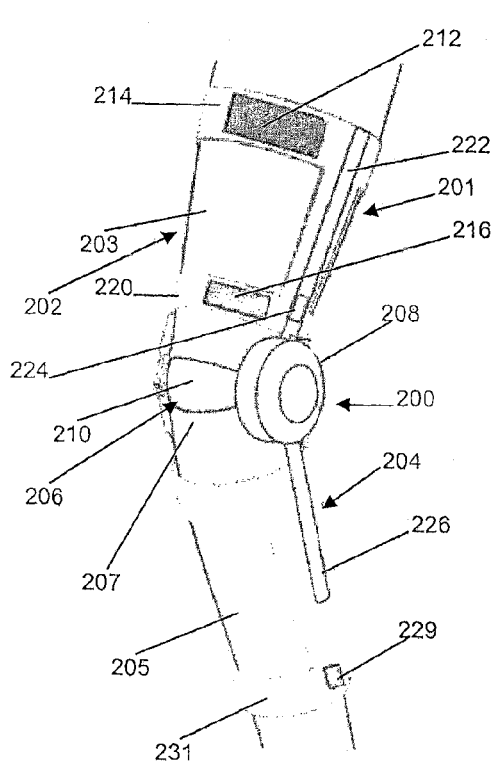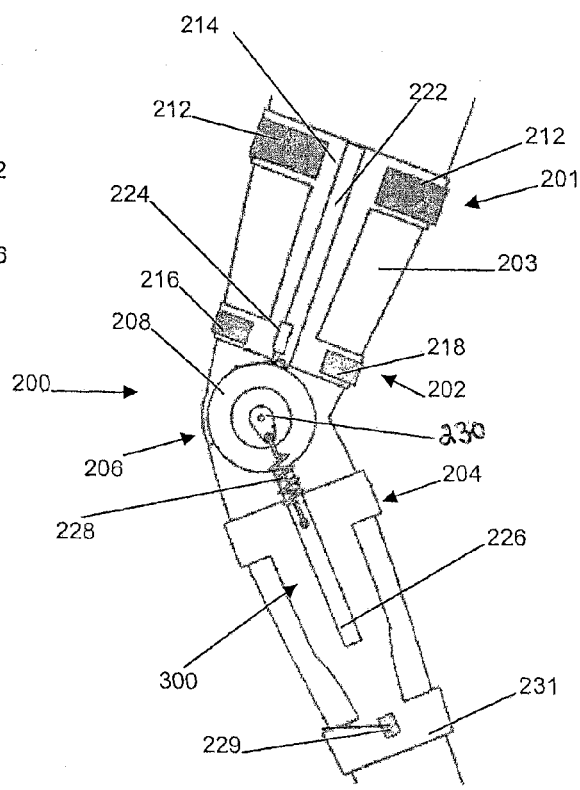
FIGURE 17
FIGURE 18

JOINT ACTUATION MECHANISM FOR A PROSTHETIC AND/OR ORTHOTIC DEVICE HAVING A COMPLIANT TRANSMISSION

This application claims priority from U.S. provisional Patent Application Ser. No. 60/878,690, filed Jan. 5, 2007, which is hereby incorporated by reference in its entirety.

FIELD OF THE INVENTION

The present invention relates to a joint mechanism for a prosthetic and/or orthotic device. More particularly, but not exclusively the present invention relates to a joint actuation mechanism for a prosthetic and/or orthotic device having a compliant transmission.

BACKGROUND OF THE INVENTION

A few types of joint actuation mechanisms for prosthetic or orthotic devices are known in the art and include joint actuation mechanisms. Usually, powered joint mechanisms form part of an orthotic device or a prosthetic device and include a housing for an actuator comprising a motor and a shaft in communication with a reducer which communicates with an output to cause the joint to rotate about an axis thereof.

A drawback of known joint actuation mechanisms include important electrical energy input to operate, affecting the autonomy of the device and requiring important battery capacity thereby affecting the weight of the device. Another drawback of know joint actuation mechanisms is that they are heavy and voluminous, directly affecting the weight and size of the device.

Some drawbacks of known knee actuation mechanisms is that they do not provide real-time direct measurement of the torque and do not demonstrate compliance in any locomotion situation, consequently the prosthetic or orthotic device to which they are mounted does not smoothly respond to the commands of a user, to unexpected events nor does it easily adapt to the specific gait style of a user.

Still another drawback of conventional powered joint actuation mechanisms is that they are relatively noisy as causing embarrassment to the user in relatively quiet social settings.

OBJECT OF THE INVENTION

An object of the invention is to provide an actuation mechanism, designed for prosthetic and orthotic application, allowing mechanical energy storage through a compliant transmission.

SUMMARY OF THE INVENTION

In accordance with an aspect of the present invention, there is provided a prosthetic device for replacing the limb of a user comprising: at least one prosthetic portion; a joint portion for being interposed between the prosthetic portion and another adjacent prosthetic portion or an adjacent limb segment of the user, the joint portion comprising a joint actuator assembly for providing the at least one prosthetic portion to pivot between flexion and extension movements relative to the another adjacent prosthetic portion or the adjacent limb segment of the user when mounted thereto; a compliant transmission assembly in operational communication with the joint portion and comprising a compliant member wherein the compliant member absorbs energy when a torque is applied between the at least one prosthetic portion and the another adjacent prosthetic portion or the adjacent limb segment of the user.

In accordance with another aspect of the present invention there is provided a orthotic device for a limb of a user, the orthotic device comprising: a proximal orthotic portion to be mounted to a proximal limb segment of the user; a distal orthotic portion to be mounted to a distal limb segment of the user; an orthotic joint portion interposed between the proximal and distal orthotic portions to be mounted to the joint of the user's limb for supporting the user's joint during flexion and extension thereof the orthotic joint portion comprising a joint actuator assembly; and a compliant transmission assembly in operational communication with the orthotic joint portion and comprising a compliant member, wherein the compliant member absorbs energy when a torque is applied between the proximal and distal portions.

In accordance with a further aspect of the present invention, there is provided a prosthetic/orthotic device comprising: at least one device portion; a joint portion for providing for the at least one device portion to pivot between flexion and extension movements relative to another adjacent device portion or an adjacent limb segment of the user; and a compliant transmission assembly in operational communication with the joint portion, the compliant transmission assembly comprising a compliant member and a pivot interposed between the compliant member and the joint portion, wherein the compliant member absorbs energy when a torque is applied between the at least one device portion and the another adjacent prosthetic portion or the adjacent limb segment of the user.

In accordance with yet another aspect of the present invention, there is provided a compliant transmission assembly for a prosthetic/orthotic device comprising at least one device portion and a joint portion for providing for the at least one device portion to pivot between flexion and extension movements relative to another adjacent device portion or tan adjacent limb segment of the user, the compliant transmission assembly comprising: a connector for being mounted to the joint portion; a compliant member mountable to the device; a pivot interposed between the connector and the compliant member; wherein the compliant member absorbs energy when a torque is applied between the at least one device portion and the another adjacent prosthetic portion or the adjacent limb segment of the user.

In accordance with yet a further aspect of the present invention, there is provided a A prosthetic/orthotic device comprising: at least one device portion; and a joint portion for being interposed between the device portion and another adjacent device portion or an adjacent limb segment of a user, the joint portion comprising:—a joint actuator assembly for providing the at least one device portion to pivot between flexion, and, extension movements relative to the another adjacent device portion or the adjacent limb segment of the user when mounted thereto, the joint actuator assembly comprising an actuator in operational communication with a first hollow shaft; and—a second sensor shaft coaxially mounted within the first hollow shaft and comprising a rotational axis sensor assembly.

In accordance with still another aspect of the present invention, there is provided a prosthetic/orthotic device comprising: at least one device portion; and a joint portion for being interposed between the device portion and another adjacent device portion or an adjacent limb segment of the user, the joint portion comprising:—a joint actuator assembly for providing the at least one device portion to pivot between flexion and extension movements relative to the another adjacent device portion or the adjacent limb segment of the user when mounted thereto;—a harmonic transmission assembly in operational communication with the joint actuator assembly; and—a sensor assembly mounted within the harmonic transmission assembly.

In accordance with still a further aspect of the present invention, there is provided a prosthetic/orthotic device comprising: at least one device portion; and a joint portion for being interposed between the device portion and another adjacent device portion or an adjacent limb segment of the user, the joint portion comprising:—a joint actuator assembly for providing the at least one device portion to pivot between flexion and extension movements relative to the another adjacent device portion or the adjacent limb segment of the user when mounted thereto; and—an actuator locking device extending outwardly of the joint portion and being in operational communication with the joint actuator assembly for providing selective locking of the joint actuator assembly.

In accordance with still yet another aspect of the present invention, there is provided a method for determining the torque of a prosthetic/orthotic device having a joint portion thereof for providing flexion and extension movements of the device, the method comprising: providing a compliant member to be in operational communication with the joint portion, providing for a deflection between the compliant member and the joint portion during the flexion and extension movements, determining the characteristics of the complaint member in operation, and determining this deflection.

In accordance with still yet a further aspect of the present invention there is provided a joint actuation mechanism for a prosthetic and/or orthotic device comprising a compliant transmission.

In accordance with yet still another aspect of the present invention there is provided a compliant transmission for a joint actuation mechanism for a prosthetic and/or orthotic device.

In accordance with yet still a further aspect of the present invention there is provided a knee actuation mechanism for a prosthetic and/or orthotic device comprising a compliant transmission.

In accordance with another aspect of the present invention there is provided a compliant transmission for a knee actuation mechanism for a prosthetic and/or orthotic device.

In accordance with further aspect of the present invention there is provided a prosthetic device comprising a joint actuation mechanism the joint actuation mechanism comprising a compliant transmission.

In accordance with still another aspect of the present invention there is provided an orthotic device comprising a joint actuation mechanism, the joint actuation mechanism comprising a compliant transmission.

In accordance with still a further aspect of the present invention there is provided a prosthetic knee device comprising a knee joint actuation mechanism, the knee joint actuation mechanism comprising a compliant transmission.

In accordance with still yet a further aspect of the present invention there is provided an orthotic knee device comprising a knee joint actuation mechanism, the knee joint actuation mechanism comprising a compliant transmission.

In an embodiment, the knee actuation mechanism of the invention comprises an actuator, a harmonic transmission assembly and a compliant torque transmission system used to serially connect the output stage (actuator and harmonic transmission) to the prosthesis structure (for example, the shank replacement part).

In an embodiment, the invention comprises a knee actuation mechanism intended to be utilized in a prosthetic device (for above-knee amputees) or an orthotic device (for users that lost control of their leg). The active device restores the normal capabilities and natural dynamics of a healthy leg for common activities such as level and incline walking, stairs ambulation as well as sitting down and up.

In an embodiment, the invention substantially restores natural dynamics and adaptation to a user's gait.

In an embodiment, the energy storing capability of the compliant transmission assembly reduce the energy required by the joint actuation system when the user is walking.

In an embodiment, the compliant transmission assembly or mechanism provides substantially the same compliance as a healthy human leg during the stance phase of the walking gait.

In an embodiment, the foregoing is achieved through a compliant element properly configured and assembled to provide the desired behavior.

In an embodiment, the compliant element comprises an elastic element.

In an embodiment, the elastic element comprises deformable and resilient characteristics.

In an embodiment, the elastic element comprises a spring.

In an embodiment, as the compliant transmission participates in providing natural dynamics, the actuator activity (which comprises an electric motor and a shaft in one example) is reduced during the stance phase, leading to reducing the power consumption for the joint actuation mechanism. In fact, the compliant transmission stores and very efficiently returns mechanical energy. Without the compliant transmission, the energy recycling process would be much less efficient as the process would involve many energy transformations (from mechanical to electrical and the opposite), thus reducing the efficiency. Therefore, the compliant transmission mechanism contributes to increasing the autonomy of the prosthetic/orthotic device and/or to reduce the dimensions and weight of the battery pack.

In an embodiment, the angular deflection of the compliant transmission is measured by means of a rotational sensor. The measurement of the deflection angle is used to provide a real-time measurement of the torque at the joint. The foregoing is impossible due to the known characteristics of the elastic element of the compliant transmission. This measurement is useful for the device's controller to provide a smoother motion (through impedance control to give but one example). This type of control better reacts to a user's commands or to unexpected events and naturally adapts to the specific gait style of a user. The mechanical compliance also contributes in improving the comfort, as shocks and vibrations are greatly adsorbed instead of being transmitted to the limb.

In an embodiment, the compliant transmission attenuates noise-generating vibrations (induced by the motor and/or harmonic transmission assembly for example), thereby substantially avoiding transmission of the vibrations to the prosthetic/orthotic device or structural elements thereof. The foregoing contributes in reducing the noise generated by the device.

In one embodiment, the center of mass of the prosthetic knee device of the invention is located proximal relative to the hip joint, the device will feel lighter by the user.

Other objects, advantages and features of the present invention will become more apparent upon reading of the following non-restrictive description of illustrative embodiments thereof, given by way of example only with reference to the accompanying drawings.

BRIEF DESCRIPTION OF THE FIGURES

In the appended drawings, where like reference numerals indicate like elements throughout and where:

FIG. 6 is a front view of the compliant transmission assembly of the invention in accordance with an embodiment thereof;

FIG. 7 is a front view of the compliant transmission assembly of FIG. 6 when the knee section of the prosthetic device is in a flexion movement;

FIG. 17 is a perspective view of an orthotic device including a joint actuation mechanism of the invention in accordance with an embodiment thereof;

FIG. 18 is a lateral schematic view of the orthotic device of FIG. 17;

DETAILED DESCRIPTION OF THE ILLUSTRATIVE EMBODIMENTS

Generally stated, the present invention relates to a prosthetic/orthotic device having at least one device portion (prosthetic or orthotic portion) and joint portion. The joint portion provides for the at least one device portion to pivot between flexion and extension movements relative to another adjacent device portion or an adjacent limb segment (such as a stump) of the user. The device includes a compliant transmission assembly in operational communication with the joint portion. The compliant transmission assembly comprises a compliant member and a pivot interposed between this compliant member and the joint portion. The compliant member absorbs energy during flexion and releases this energy during extension. When absorbing energy, the compliant member dampens flexion and when releasing energy, compliant member assists extension.

With reference to the appended drawings illustrative embodiments of the present invention will now be described so as to exemplify the invention only and by no means limit the scope thereof.

Prosthetic Device

Figure 1:
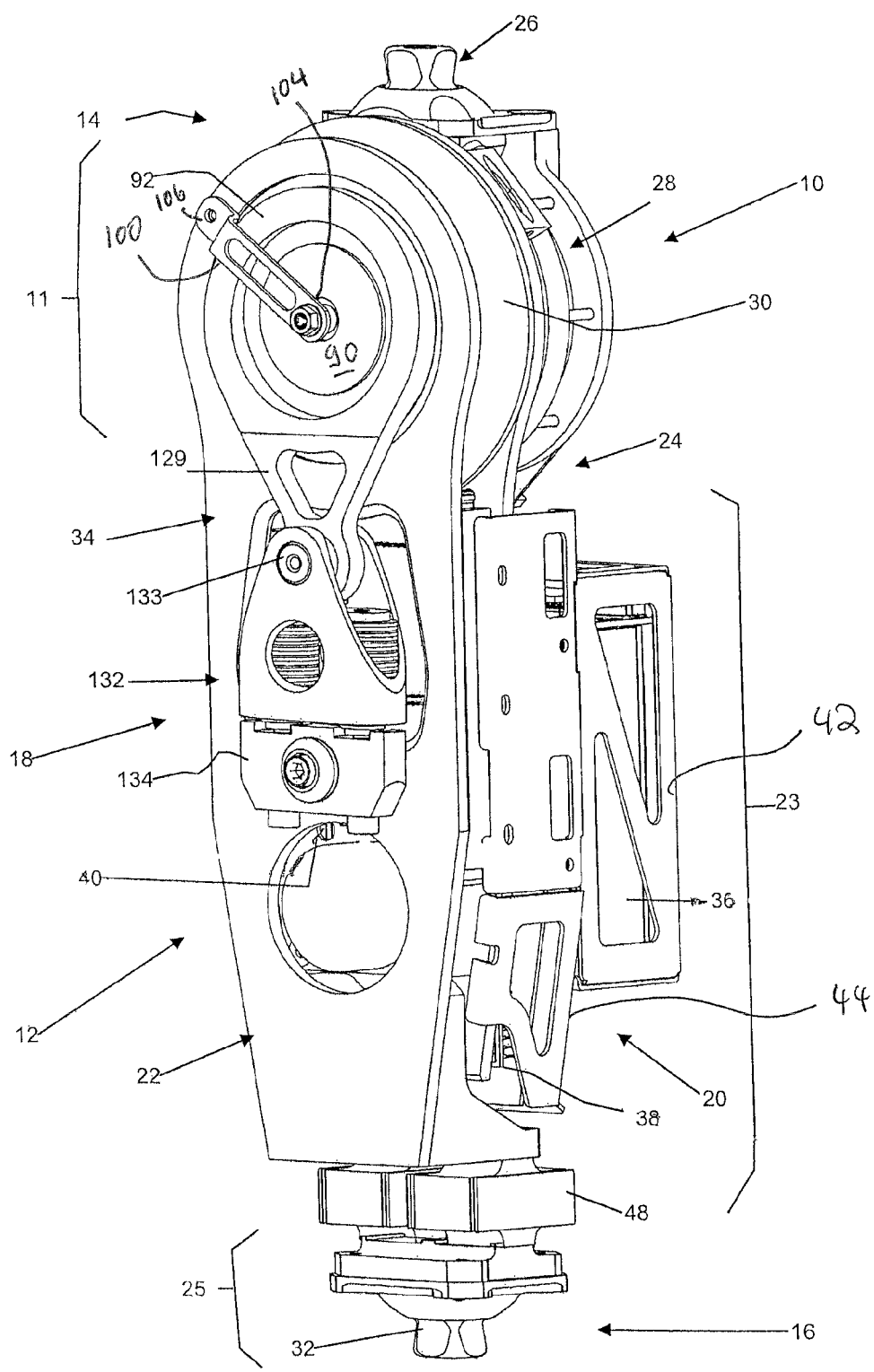
FIG. 1 is a perspective view of prosthetic device including the joint actuation mechanism of the present invention in accordance with an embodiment thereof.
Figure 2:
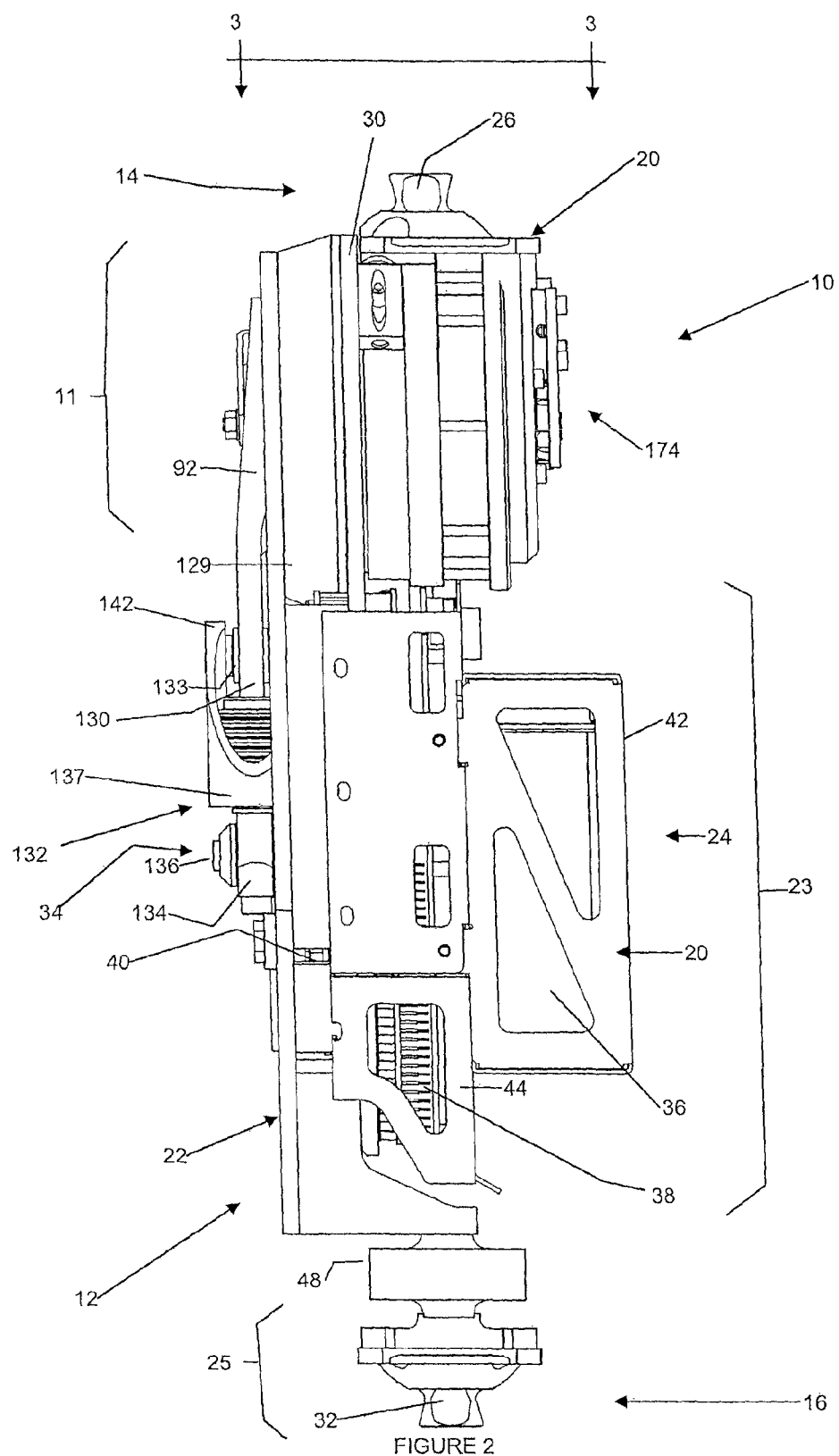
FIG. 2 is a front view of the prosthetic device of FIG. 1.

FIGS. 1 and 2 show a joint mechanism 10 in accordance with an embodiment of the present invention. In this example the powered joint mechanism 10 is a knee joint mechanism The knee joint mechanism 10 is mounted to and forms part of a prosthetic device 12. The prosthetic device 12 is a lower leg structure or shank structure 12 having a top end and bottom end, 14 and 16, respectively, front and rear face's 18 and 20 respectively and lateral sides 22 and 24. More specifically, the prosthetic lower leg structure 12 defines a knee joint portion 11, a prosthetic shin, portion 23 and a prosthetic ankle portion 25 (only a reference to an area not an ankle per se, which is not shown). The knee actuation mechanism 10 includes a prosthetic connector 26 at the top end 14 which sits on an actuator assembly 28 that in turn is mounted to a rotatable knee shank structure 30. It should be noted here that the rotatable knee shank structure 30 includes the knee portion 11 of the shank structure 12 as well as the actuator assembly 28, thus the knee shank, structure 30 (excluding the actuator assembly 28) is integral with the shank structure 12. The prosthetic connector 26 is configured to be connected to a common socket (not shown) that is mountable to the leg stump of a user. The shank structure 12 includes a distal connector at the bottom end 16 (or ankle portion 25) for connecting a common prosthetic ankle, and foot product thereto (not illustrated).

As will be discussed herein the knee actuation mechanism 10 includes a compliant transmission assembly 34 mounted to the knee portion 11 and the shin portion 23 of prosthetic lower leg shank structure 12.

The prosthetic lower leg shank structure 12 also includes an electronic assembly comprising a power board 40, an I/O board 38 and a battery 36 all of which are respectively held by covers 42, 44 to the shin portion 23 of prosthetic shank structure 12. Inertial sensor boards (not shown) are located respectively on the shin portion 23 of the prosthetic shank structure 12 and load cells or floor contact switches 48 are located at bottom end 16 (ankle portion 25).

Actuator Assembly

Figure 3:
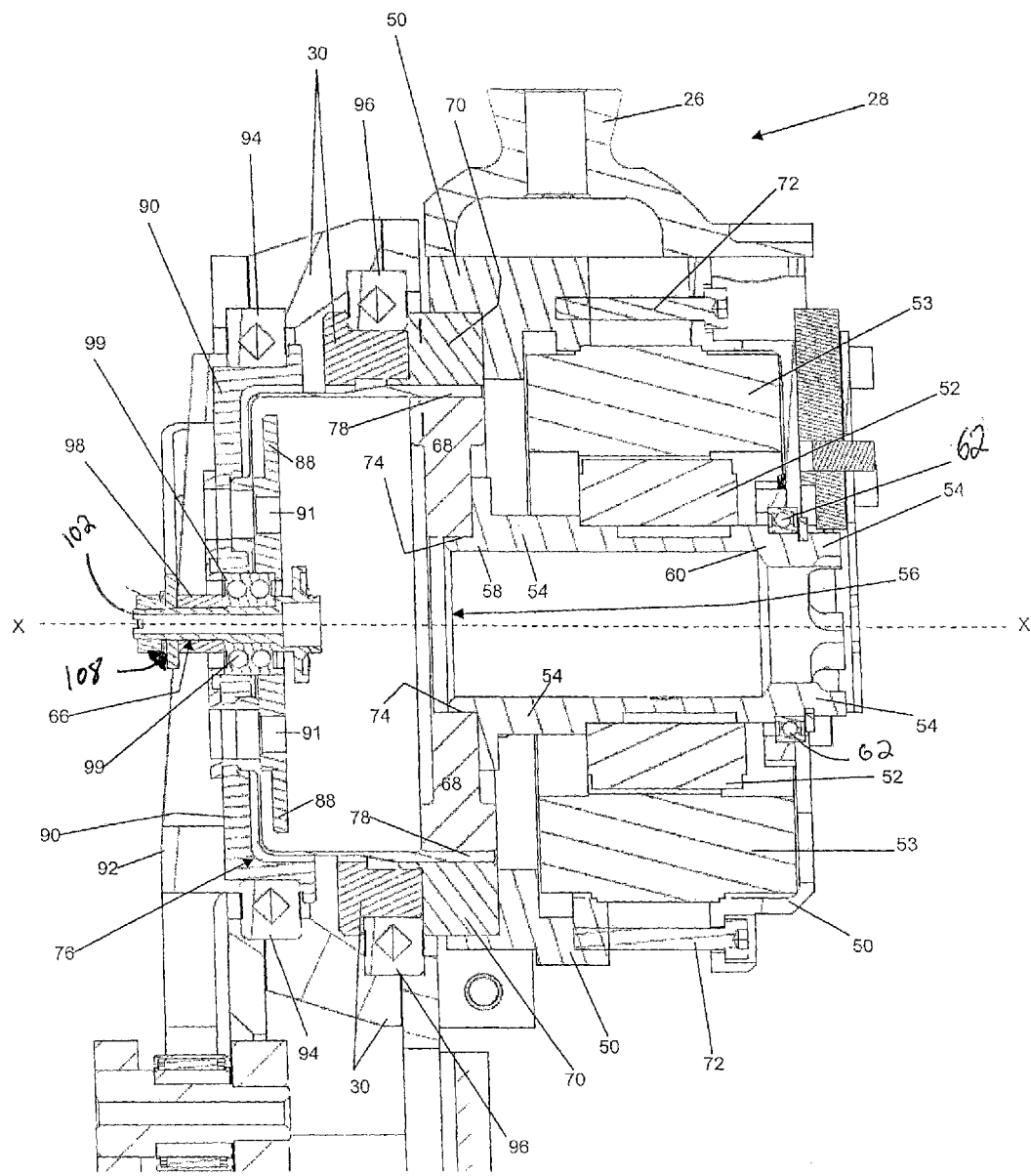
FIG. 3 is a sectional view of the actuation assembly of FIG. 2 along line 3-3 thereof excluding the sensor assembly of the invention.

With particular reference to FIG. 3, the actuator assembly 28 will now be described.

The actuator assembly 28 includes an actuator housing 50 for housing an actuator 52, which can be a motor rotor for example, such as a Brushless DC motor in a particular non-limiting example, rotatably mounted within a stator 53.

Actuator 52 is in operational communication with a first hollow shaft 54 defining the knee rotation axis X between flexion and extension. Shaft 54 is directly connected to a harmonic transmission assembly 56 (in the form of a harmonic drive gearing) at one end 58 thereof, while the floating end 60 is guided by ball bearings 62 mounted to the housing 50.

The shaft 54 is hollow, as such second shaft 64 (see FIG. 5) is inserted therein but it should be noted that shaft 54 does not act on shaft 64 but merely rotates thereabout.

In this non-limiting example, the harmonic transmission assembly 56 includes a wave generator 68 whose locational and rotational guidance is ensured by a circular spline 70 which is mounted to the actuator housing 50 via fasteners, glue, press fitting and the like. More specifically, the wave generator 68 is an assembly of bearings in a steel disk plug having a generally elliptical outer shape and including a central aperture 74 for operatively receiving the shaft 54 therethrough.

Figure 4:
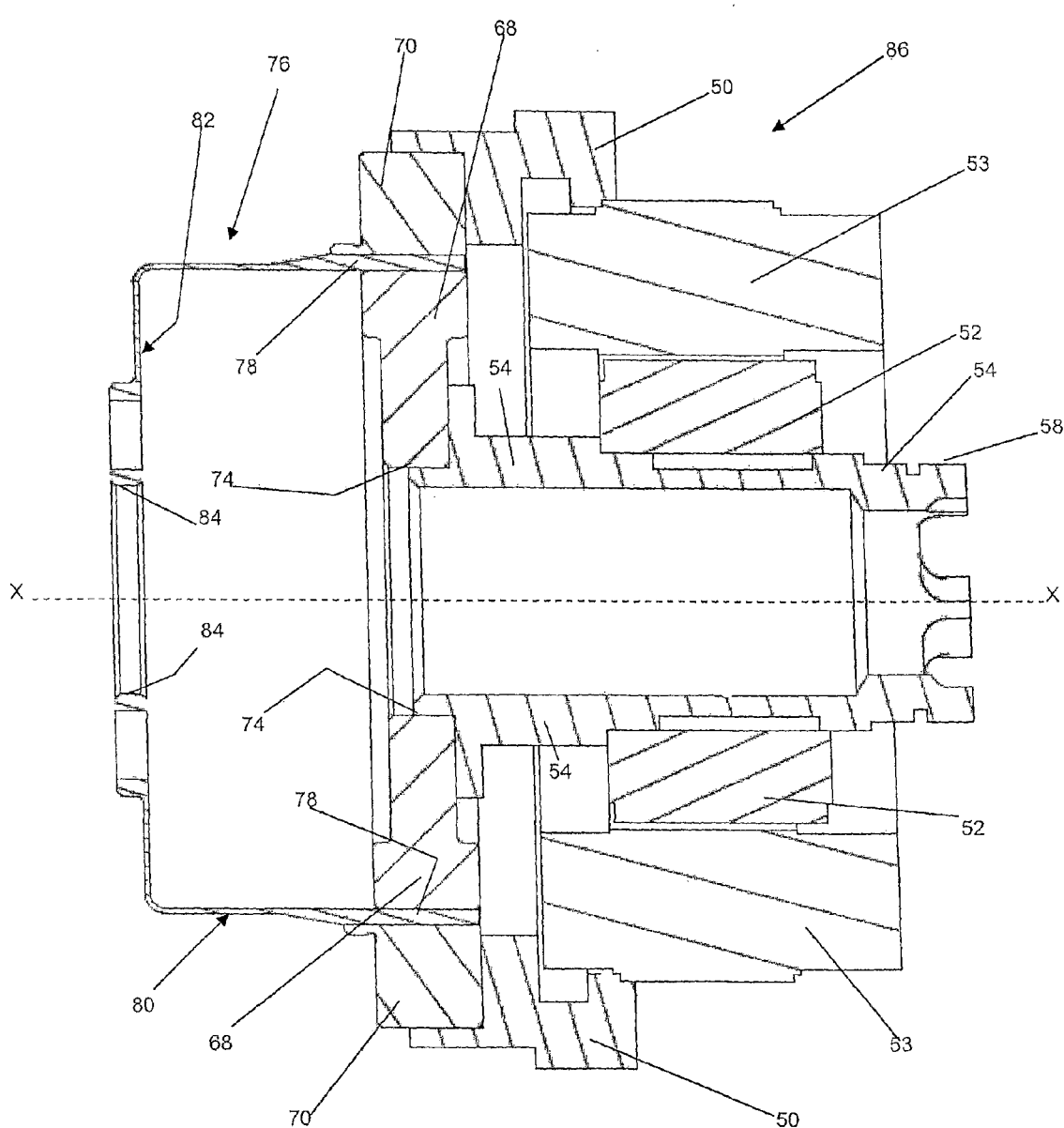
FIG. 4 is a simplified view of a portion of FIG. 3.

With reference to FIGS. 3 and 4, the harmonic transmission assembly 56 also includes a flexspine 76 having one end 78 mounted between the wave generator 68 and the circular spline 70 and defining a brim composed of gear teeth. A flexible cup portion 80 extends from the brim end 78 to define an opposite end 82 having an aperture 84 (see FIG. 4).

In general, the flexspline 76 comprises a thin-walled steel cup 80 with gear teeth machined on the outer surface of the brim end 78. When the harmonic transmission assembly 56 is assembled, the wave generator 68 is inserted inside the flexspline 76 such that the bearings are at the same axial location as the flexspline 76 gear teeth. The flexspline 76 wail near the brim end 78 conforms to the same elliptical shape of the wave generator 68 outer surface providing the flexspline 76 to have an elliptical gear pitch on its ouster surface. The flexspline 76 and more specifically, the flexible cup 80 is the output member of the harmonic transmission assembly 56 and is mounted to the compliant transmission assembly 34 as will be explained herein. In general, the circular spline 70 is a rigid circular steel ring with teeth on the inside diameter. The circular spline 70 is located such that its teeth mesh with those of the flexspline 76.

Of course, other types of harmonic transmission assemblies can be used within the context of the present invention.

Turning now to FIG. 4 in order to simplify and recapitulate the foregoing, the motor rotor 52 and the harmonic transmission assembly 56 define a reducer assembly 86. The stator 53 and the circular spline 70 are connected together via the actuator housing 50 which is connected to the prosthetic connector 26 as shown in FIGS. 1, 2 and 3. The motor rotor 52 is directly inserted onto first shaft 54 which connects to the wave generator 68 via shaft-receiving aperture 74 and bolts (not shown). The output stage of the transmission is the flexible cup portion 80 of the flexspline 76, which as mentioned above, connects to the compliant transmission assembly 34.

In one non-limiting example, the reducer assembly 86 provides a reducing ratio of 51:1 between the input stage and the output stage of the actuator assembly 28. Of course, as the skilled artisan will readily contemplate, different transmission ratios are available for this type. of transmission, but a relatively low ratio leads to lower motor 52 rotational speed, therefore helping to maintain low mechanically generated noise and reducing the inertia of motor rotor 54 in respect to the output, stage. In one embodiment, a low inertia is desirable to reduce the kinetic energy of the knee actuation mechanism 10 and to provide a faster response time.

With reference again to FIG. 3, the output end or output stage of the actuator assembly 28 will now be described in greater detail.

The flexspline 76 is secured in place between a backing plate 88 and a retaining cover 90 both of which are fastened together via fasteners 91 such as dowell pins for example. The rotational motion of the flexspline 76 is transmitted to the compliant transmission assembly 34 via the retaining cover 90 which is connected to the lever 92 (which can be any type of cam or like member) of the compliant transmission assembly 34 as will be discussed herein. The flexspline retaining cover 90 is guided during rotation thereof about axis X by cross-roller bearings 94, which are mounted to the knee shank structure 30. Therefore as the retaining cover 90 turns, it turns the lever 92 in unison therewith.

Figure 5:
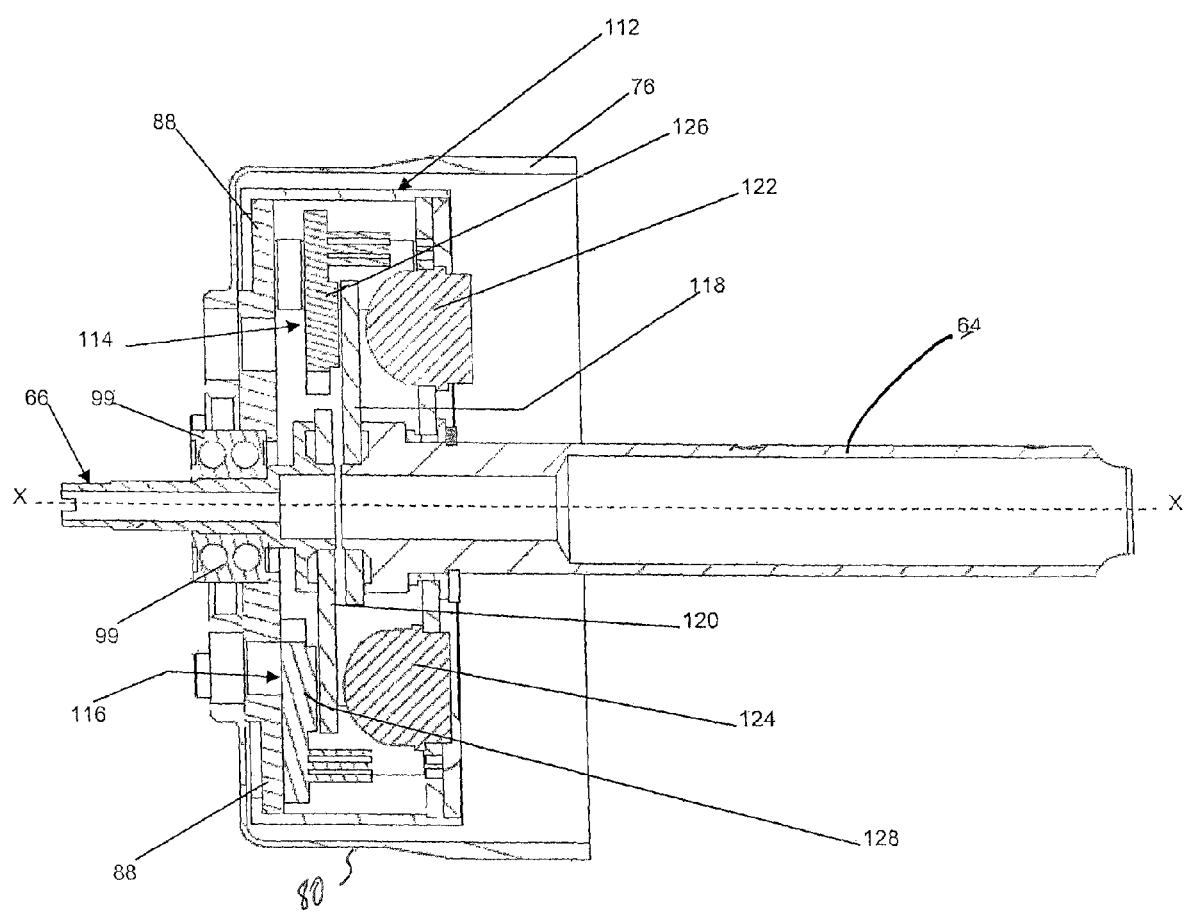
FIG. 5 is another simplified view of a portion of FIG. 3 including the sensor assembly of the invention in accordance with an embodiment thereof.

Referring to FIG. 5, the second shaft 64 runs through the wave generator 68 into the flexible cup 80 and is in communication with a sensor assembly 112 within the flexible cup 80 as will be discussed herein.

Referring to FIGS. 3, 4 and 5, the sensor assembly 112 is also in communication with a third shaft 66 within the flexible cup 80, this third reference shaft 66 exits the flexible cup 80 via aperture 84 and into a tubular member 98. The third reference shaft 66 is guided by double-row ball bearings 99.

With reference to FIGS. 1 and 3, an elongate connector 100 is securely mounted to the free end 102 of the third shaft 66 at one end 104 thereof and to the knee shank 30 (knee joint portion 11) at an opposite end 106 thereof. In this way, as the knee shank 30 (and effectively the entire shank 12) rotates about axis X, the elongate connector 100 turns this third shaft 66 in unison. The connector 100 is fixedly mounted to the shaft 66 via a nut and washer assembly 108. It should be noted that the elongate connector 100 is so configured as to provide a clearance for the compliant transmission lever 92.

Torque Sensor and Rotational Axis Sensor

With reference to FIG. 5, the knee rotational axis sensor assembly 112, mentioned above and in accordance with an embodiment of the invention will be herein described.

The sensor assembly 112 comprises two rotational sensors 114 and 116. In one non-limiting embodiment, the sensors 114 and 116 are one-turn absolute optical type and comprise of a respective partial disk 118 and 120, a respective light emitter 122 and 124 as well as a respective sensor element 126 and 128. The sensor element 128 measures the relative displacement between the knee shank structure 30 and the output stage (the flexible cup 80) of the harmonic transmission assembly 56. This displacement corresponds to the angular deflection of the compliant transmission assembly 34 (which will be discussed below).

The partial disk 120 is attached to the third shaft 66 which is connected to the shank structure 30 via connector 100, the light emitter 124 and the sensor element 128 are attached to the flexible harmonic transmission output (the flexible cup 80).

The partial disk 118 is attached to the second shaft 64, while the light emitter 122 and the sensor element 126 are attached to the harmonic transmission output (flexible cup 80).

Figure 5A:
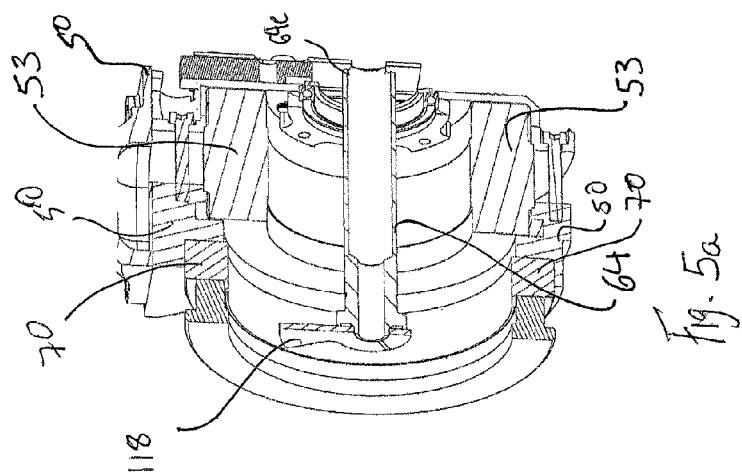
FIG. 5a is a perspective view of the stator assembly of the joint actuation mechanism of FIG. 1 in accordance with an embodiment of the invention.
Figure 5B:
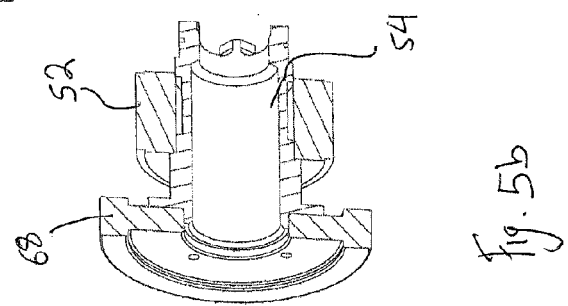
FIG. 5b is a perspective view of the motor rotor assembly of the joint actuation mechanism of FIG. 1 in accordance with an embodiment of the invention.
Figure 5C:
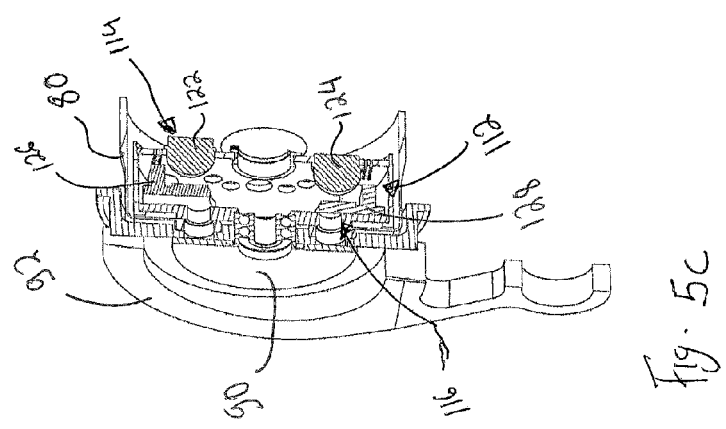
FIG. 5c is a perspective view of the transmission output assembly of the joint actuation mechanism of FIG. 1 in accordance with an embodiment of the invention.

When rotating the motor rotor 52 and, shaft 54 assembly produce a relative rotational motion between the stator 53 and the transmission, output assembly (see FIG. 5c). This relative motion is measured with the sensor partial disk 118 and its sensor detector element, 126.

The motion of the transmission output assembly (see FIG. 5c) tends, to transmit the movement to the shank 30 through the compliant transmission 34. If the shank 30 resists to the movement (acceleration or external force on the shank structure 12), the compliant transmission 34 will be deflected. The deflection of the compliant transmission 34 creates relative rotational movement between the transmission output assembly (see FIG. 5c) and the shank structure 12. This relative motion is measured with the sensor partial disk 120 and its sensor detector 128 thereby providing a torque sensor.

Of course, the skilled artisan will readily appreciate that other types of sensors (such as magnetic sensors, optical sensors, potentiometers) could be used within the context of the present invention. Sensors with relative displacement measurement instead of absolute displacement could also be used. Furthermore, the skilled artisan can position the sensor that measures the deflection of the compliant transmission assembly 334 (i.e., the torque sensor) in a different location, for example in a linear position on the spring assembly (which will be described herein).

With reference to FIGS. 5a, 5b, 5c and 5d the foregoing will be summarized for clarity purposes only.

FIG. 5a shows the stator assembly which includes the motor stator 53, the second shaft 64 and the circular spline 70. Stator 53 which as aforementioned is fixed to the housing 50. Second shaft 64 carries the sensor partial disk 118 of sensor 114 at one end thereof and is linked to the housing 50 at another opposite end 64e thereof. The circular spline 70 is also mounted to the housing 50.

FIG. 5b shows the motor rotor assembly which includes the motor 52, the motor shaft 54 and the wave generator 68.

FIG. 5c shows the transmission output assembly which includes the flexible cup 80, both sensors 114 and 116 of the sensor assembly 112 which are mounted within the flexible cup 80 and the lever 92 of the compliant transmission assembly 34 (that will be discussed in greater detail below) which is mounted to the flexible, cup 80 via retaining cover 90. The sensors 114 includes the light emitter 122 and the sensor element 126 and the sensor 116 includes the light emitter 124 and the sensor element 128.

Figure 5D:
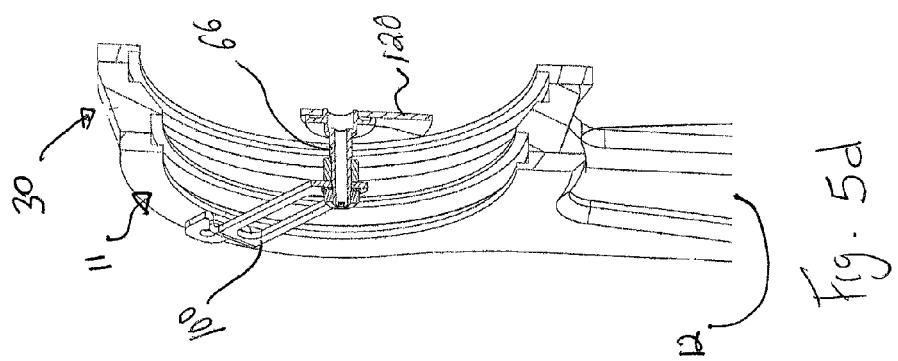
FIG. 5d is a perspective view of the shank assembly of the joint actuation mechanism of FIG. 1 in accordance with an embodiment of the invention.

FIG. 5d shows the shank assembly including the shank structure 12 (in this case only the knee portion 11—which is included in the knee shank structure 30 as explained above—is shown), a connector 100 fixedly mounted to the third shaft 66 at one end thereof, with the other end of the shaft 66 carrying the sensor partial disk 120 of sensor 116. Referring back to FIG. 5, when FIGS. 5a to 5b are assembled the partial disks 118' and 120 are respectively positioned between sensor element, 126 and light emitter 122 and between sensor element 128 and light emitter 124.

Compliant Transmission Assembly

Turning now to FIGS. 1, 6 and 7, the compliant transmission assembly 34 will be described herein.

The compliant transmission assembly 34 comprises a connector in the form of a generally circular lever 92 that is connected to the retaining cover 90 so as to move in unison with the knee shank structure 30 (which is discussed is integral to the shank structure 12). The lever 92 has a bottom extension 129 defining a lower end 130 movably, and in this case pivotally, mounted to a compliant member in the form of a spring assembly 132 via pivot 133. The spring assembly 132 is mounted to the shin portion 23 of the shank structure 12 through a quick connecting, mechanism 134 mounted to shank structure 12 via an attachment pin or pivot 136. The spring stack assembly 132 comprises a spring-carrying body 137.

Figures 8, 9:
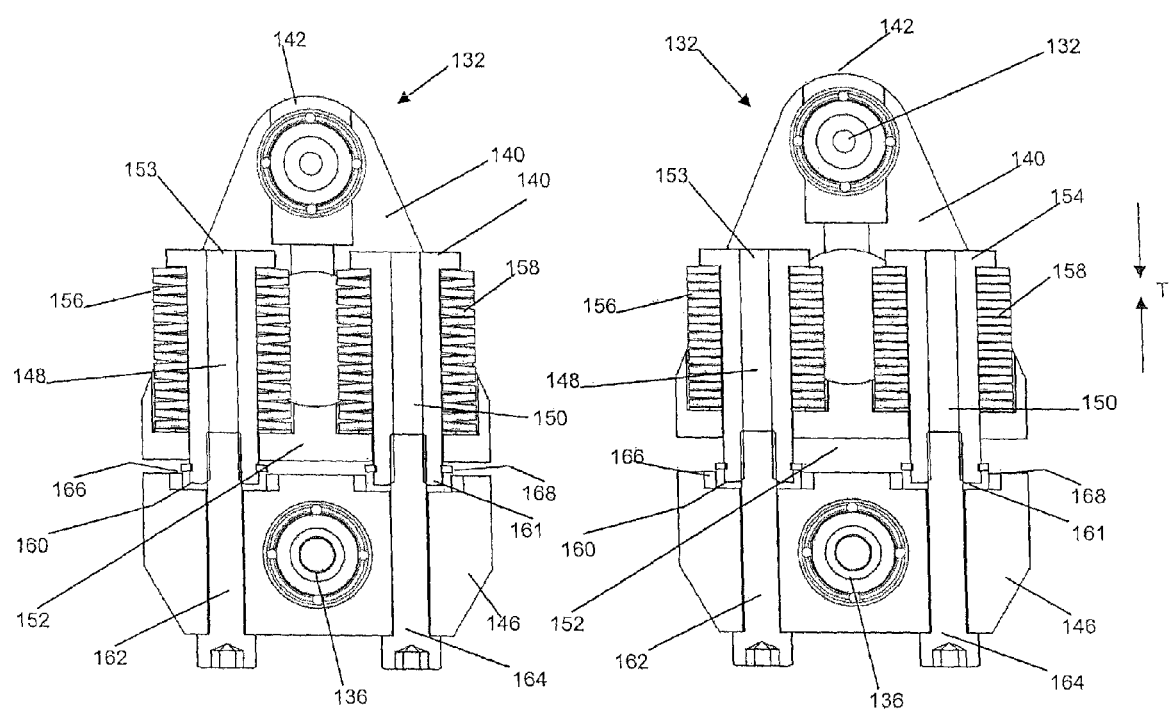
FIG. 8 is partial front view of the compliant transmission assembly of FIG. 6.
FIG. 9 is a partial front view of the compliant transmission assembly of FIG. 7.

With reference to FIGS. 8 and 9, the spring-carrying body 137 comprises an outer body portion 138 (see FIGS. 6 and 7) and an inner body portion 140 both of which have respective top extensions defining a top end 142 for pivotally mating with the bottom end 130 of the lever 92 via pivot 133. The quick connecting mechanism 134 comprises an outer body portion 144 (see FIGS. 6 and 7) and an inner body portion 146. A stress member in the form of a pair of stress tubes 148 and 150 are mounted to the body portion 140 and respectively sandwich, between their mutual lower platform 152 and their respective top t-formations or shoulders 153 and 154, a respective compliant element, in this example, being a spring stack 156 and 158 (see FIGS. 8 and 9). The respective bottom portion 160 and 161 of each stress tube 148 and 150 is configured to receive a respective stress actuator in the form of screws 162 and 164 and includes a respective retaining ring 166 and 168 mounted thereto. Therefore, the stress tubes 148 and 150 and retaining rings 166 and 168 provide a predetermined high pre-stress to the spring stack assembly 132. This pre-stress is accentuated by the screws 162 and 164 during assembly. It is also possible to adjust the spring stiffness by tightening or loosening the screws 162 and 164, this could help accommodate users of different weights, as the ideal stiffness would be higher for heavier users and lower for lighter users.

In one embodiment, the spring stacks 156 and 158 can be made from a limited displacement dual stack of Belleville washers. Of course, the skilled artisan will readily comprehend that other configurations could include a different or equivalent number of stacks, comprised of either Belleville washers, helicoidal springs, machined springs, rubber stacks or any other component composed of any other material that could provide the desired behavior within the context of the present invention.

Figures 10, 11:
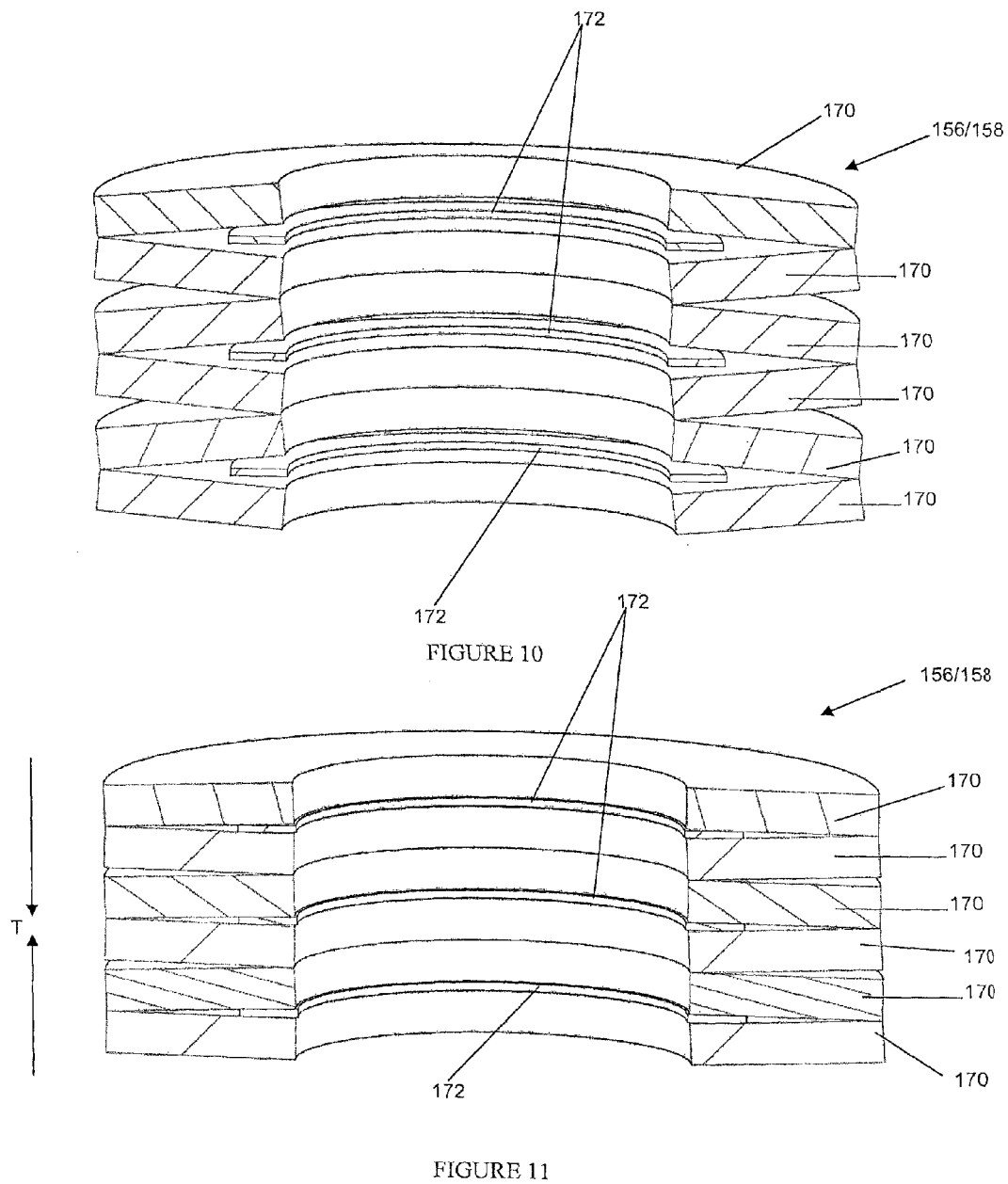
FIG. 10 is a partial front view of a compliant element of the compliant transmission assembly of FIG. 6.
FIG. 11 is a partial front view of a compliant element of the compliant transmission assembly of FIG. 7.

With respect to FIGS. 10 and 11, in the present non-limiting example, each spring stack 156 and 158 is comprised of seventeen Belleville washers 170 (only six shown here) placed back to back. Other implementations could include a different number as well as different types of washers 170 to accommodate different ranges of user weights. Between each pair of Belleville washers 170 is placed a spacer 172 that is used to limit the deflection of the washers 170 so as to control the maximum deflection angle of the compliant transmission and to extend the fatigue life of the springs 156 and 158.

Figure 12:
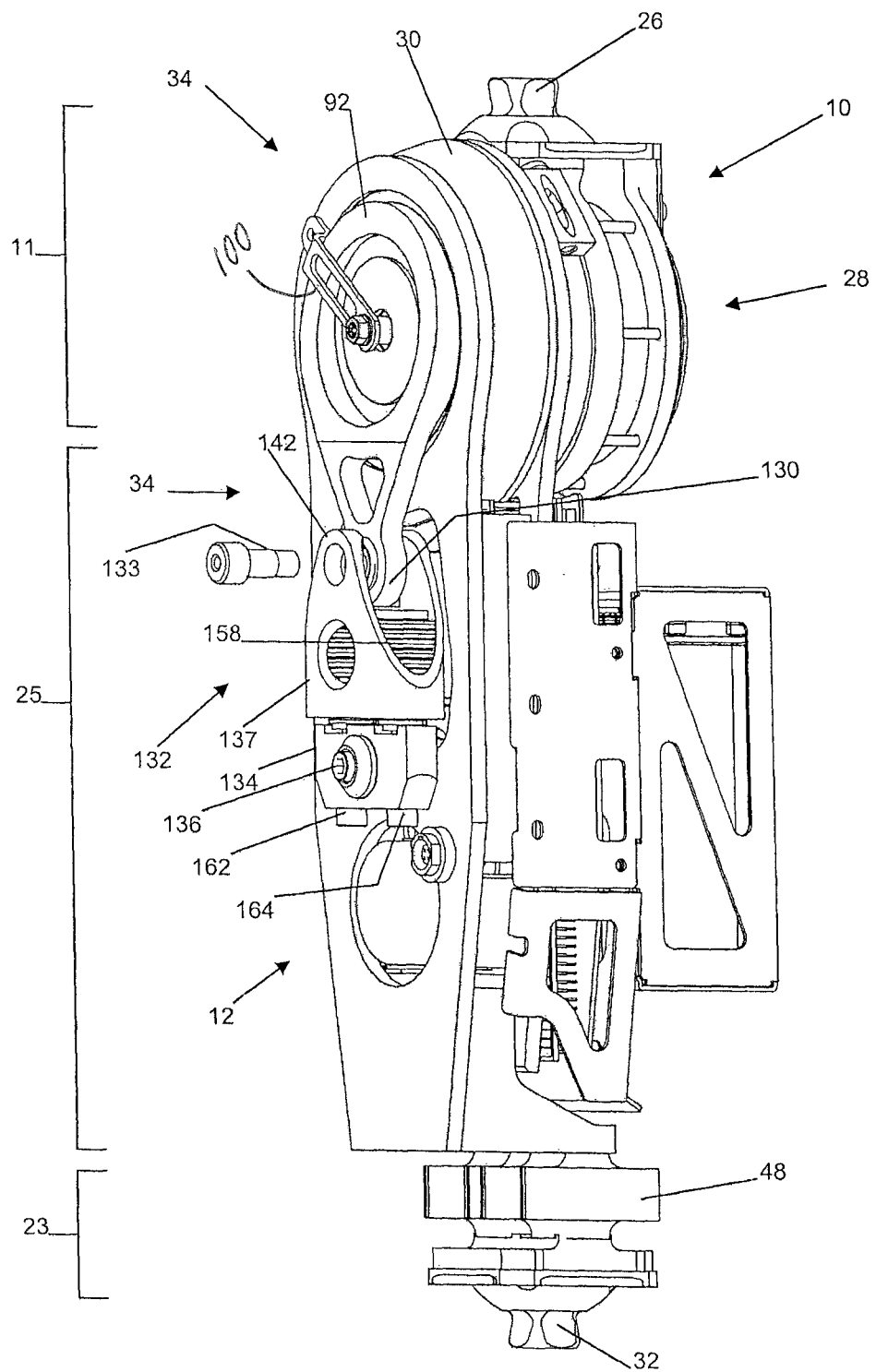
FIG. 12 is another perspective view of the prosthetic device of FIG. 1.

Turning now to FIG. 12, the compliant transmission assembly 34 provides for disengaging the spring assembly 132 from compliant transmission lever 92. The foregoing provides for the free swing mode which be useful when the prosthesis runs out of power, as the knee actuation mechanism 10 would demonstrate an important resistance to movement, making walking quite strenuous. With the spring assembly 132 disengaged, the compliant transmission lever 92 is freed and the knee actuation mechanism 10 becomes unrestrained for rotation. A passive mechanism applying resistance to the rotation motion could be added to obtain a more appropriate behavior. To detach the spring stack assembly 132 and enter the free swing mode from the lever 92, tension in the screws 162 and 164 is released and the pivot 133 removed.

Actuator Locking Device

Figure 13:
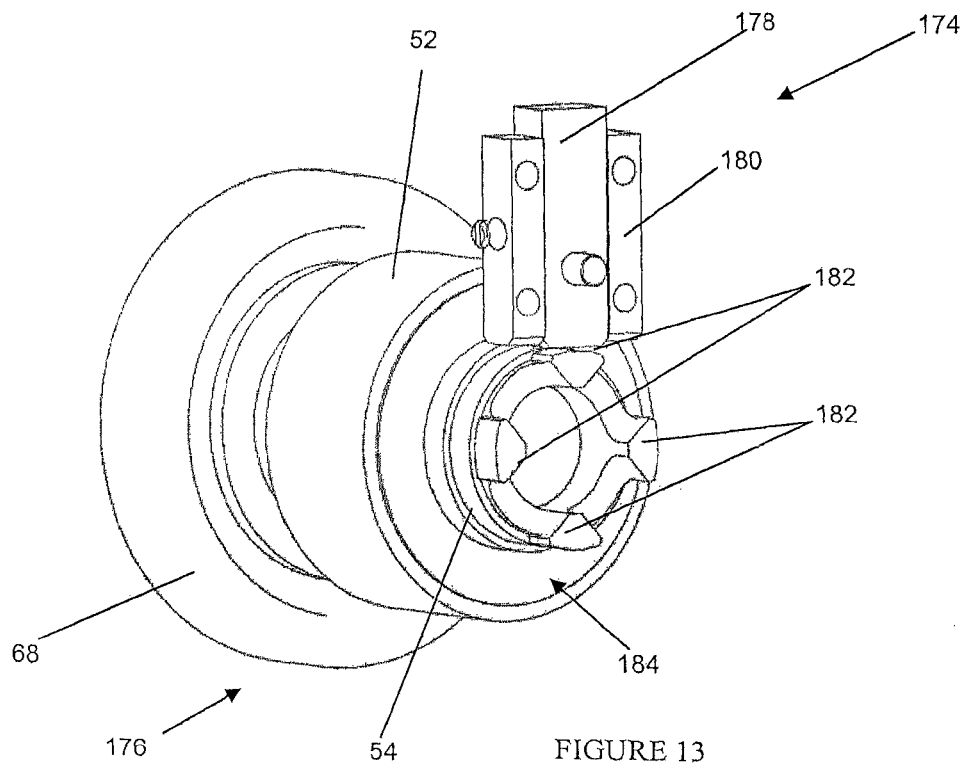
FIG. 13 is a perspective view of the locking device of the joint actuation mechanism of FIG. 1 in an unlocked position.
Figure 14:
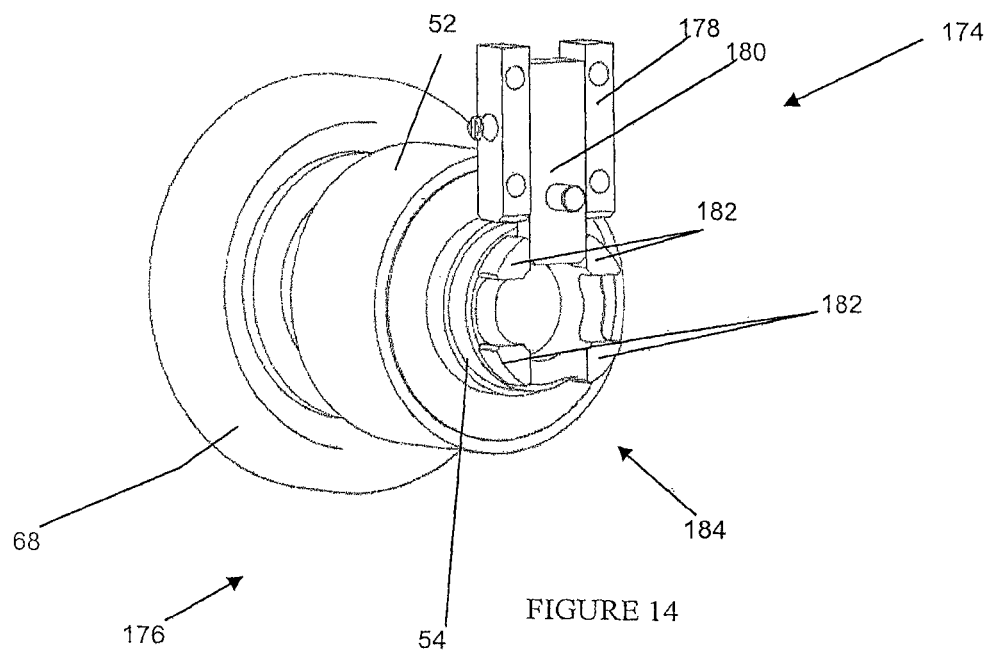
FIG. 14 is a perspective view of the locking device of the joint actuation mechanism of FIG. 1 in a locked position.

With reference to FIGS. 13 and 14, the knee actuation mechanism 10 also includes a locking device 174 which allows for manually locking the knee joint actuation mechanism 10 at a desired knee angle. As shown in FIG. 2, the locking device 174 is positioned on lateral side 24 of the knee portion 11 of the shank structure 12. FIGS. 13 and 14 respectively show a simplified view of the motor assembly 176 and of the locking device 174 in unlocked operation and in locked operation. The motor assembly 176 comprises the motor rotor 52, the shaft 54 and of the wave generator 68 of the harmonic transmission assembly 56. The locking device 174 comprises a locking slider 178 and a locking slider guide 180. When the locking device is engaged, the locking slider 178 engages between teeth 182 located at the extremity end 184 of the shaft 54.

The foregoing provides locking the input stage (i.e. motor 52, shaft 54, and wave generator 68 of the harmonic transmission assembly 56) at predetermined angles determined by the configuration of the teeth 182. In this non-limiting example, the predetermined angles are at every 90 degrees of rotation about the axis X. In the case where the harmonic transmission ratio is 51:1, a 90 degree locking angle provides for the output stage of the harmonic transmission assembly 56 to be blocked at every 1.76 degrees of rotation about the axis X.

The ability to lock the knee joint mechanism 10 at multiple angles provides for the user to increase comfort for activities such as standing for extended periods or other activities requiring locking of the knee joint mechanism 10. In one non-limiting embodiment, the locking device 174 includes locking of the input stage of the harmonic transmission 56 at higher or smaller portions of a rotation about the X axis, as such the number of teeth 182 of the shaft 54 and the size of the slider 178 are designed accordingly. In another non-limiting embodiment, the locking device 174 includes a frictional braking, system (not illustrated), allowing locking at any desirable angle.

Therefore, the knee actuation mechanism 10 comprises an actuator assembly 28, a harmonic transmission assembly 56 and a compliant transmission assembly 34.

Operation

In operation, the motor 52 actuates the shaft 54, which rotates about axis X, causing the wave generator 68 to rotate therewith, thereby actuating the flexspline 76 (and hence the flexible cup 80) and consequently reducing the rotation movement, movement that is transmitted from the flexspline 76 to the circular spline 70. The circular spline 70 being connected to the housing 50 causes the rotation of the knee shank structure 30 (and consequently of the shank structure 12) about axis X and in accordance with this reduced transmitted rotational movement, between flexion and extension of the knee joint actuation mechanism 10 (depending on the rotational direction of the shaft 54 as the skilled artisan will readily understand).

As the housing 50 rotates, the second shaft 64 being linked thereto will rotate along therewith, thus, rotating the sensor of partial disk 118, providing the sensor assembly 112 to detect the position or angle of the stator assembly relative to the transmission output assembly (as described above).

As the flexspline 76 rotates about axis X, the reduced movement thereof is transferred to the lever 92, since it is connected to the simultaneously rotating flexspline cover 90, causing lever 92 to rotate therewith.

The rotation of the lever 92 causes a deflection between the lever 92 and the spring assembly 132 about pivot 133. This aforementioned deflection will depend on whether the movement of the shank structure 12 originates from the motor 52 or from the user (not shown).

When the movement of shank structure 12 originates from the motor 52 as described above and the shank structure 12 rotates about X in the direction shown by R1 in FIG. 7, during flexion, the lever 92 is rotating along with the flexspline 76 (in direction R1) and as such pulls on the spring assembly 132 causing the springs 156 and 158 to contract (as shown by arrow T in FIG. 11), thereby causing pivot 133 to deflect in the direction shown by D1 (towards the left). In this way, the compliant transmission 34 pulls the shank structure 12 towards direction R1. When the shank structure 12 rotates about X in the direction shown by R2 in FIG. 7, during extension, the lever 92 is rotating along with the flexspline 76 (in the direction shown by R2) and pulls on the spring assembly 132 causing the springs 156 and 158 to contract (as shown by arrow T in FIG. 11), thereby causing pivot 133 to deflect in the direction shown by arrow D2 (towards the right). In this way, the compliant transmission 34 holds back the shank structure 12 as it moves in direction R1.

When the movement of the shank structure 12 originates from the user (i.e. when motor 52 is not in function and as such the flesxpsline 76 and by extension the lever 92 are idle), the operation of the compliant transmission assembly is as follows. If the user wants to cause a flexion movement (R1), they apply a force to the shank structure 12 via their limb stump, this force (torque) causes the shank structure to move in the direction shown by arrow R1 (flexion), the shin portion 23 of the shank structure 12 moves before the knee portion 11, hence, the lever 92 resists the movement of the shin portion 23, causing the springs 156 and 158 to compress (T) and causing a deflection of pivot 133 in the D2 direction (towards the right). If the user wants to cause an extension movement (R2), they apply a force to the shank structure 12 via their limb stump, this force (torque) causes the shank structure 12 to move in the direction shown by arrow R2 (extension), the shin portion 23 of the shank structure 12 moves before the knee portion 11, hence, the lever 92 resists the movement of the shin portion 23, causing the springs 156 and 158 to compress (T) and causing a deflection of pivot 133 in the direction shown by D1 (towards the left). Hence, in these cases, the lever 92 impedes the movement of the shank structure 12. The same occurs during normal walking or any type of heel strike or standing. As soon as there is a force, (torque) applied to the shank structure 12, the compliant transmission assembly 34 will resist this movement. Thereby adding rigidity to the shank structure 12 during standing or a more fluid and less abrupt movement.

Therefore, the presence of the compliant element (the action of springs 156 and 158) between the actuator output and the prosthetic shank structure 12 allows fore relative motion of the knee section 11 about the knee axis X, without necessarily requiring motor motion. In one embodiment, deflection of the compliant element is limited to a range of about ±1.5 degrees with respect to the compliant transmission lever 92 position. The non-linearity of springs 156 and 158 is either defined through appropriate spring behavior or spring assembly length, or compliant transmission lever 92 length, or by design.

In general, the design of both the behavior and deflection limit of the compliant transmission assembly 34 with respect to a prosthetic knee actuation mechanism 10 is substantially based on human leg dynamics. The stiffness of the normal healthy human leg during the whole stance phase including heel strike changes with ambulation speed. The faster the walking speed, the stiffer the knee joint is. The maximum spring 156 and 158 deflection (1.5 degrees) corresponds approximately to the maximum deflection angle of the human knee during walking. The stiffness of the human leg also increases with body mass. In one embodiment, the stiffness of the springs 156 and 158 should substantially match the user's weight.

Figure 15:
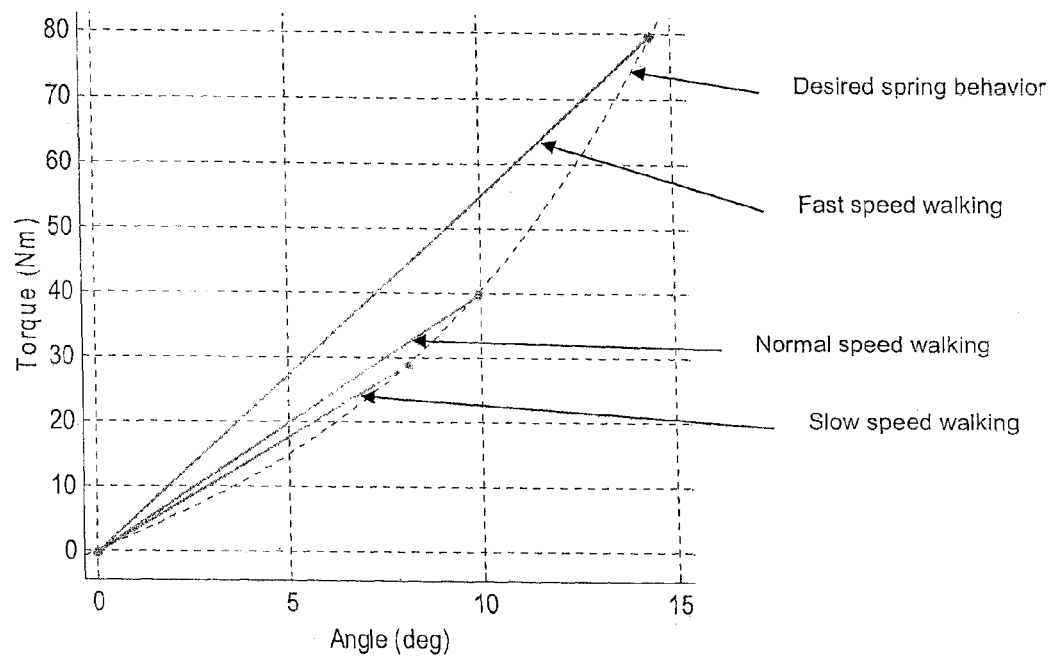
FIG. 15 is a graph showing the desired compliant element behavior of the joint actuation mechanism of FIG. 1 on the stiffness of the normal human knee joint at different walking speeds.

The graph in FIG. 15 shows the desired compliant element (spring 156 and 158) behavior based on the stiffness of the normal human knee joint at different walking speeds.

Presence of the springs 156 and 158 at this level off the compliant assembly 34 allows to quantify net torque (R1 or R2) through measurement of the relative angle between the shank structure 12 and harmonic transmission output (the flexspline 76/flexible cup 80). The sensor assembly 122, in the knee actuation mechanism 10 provides for torque measurement. Torque measurement is advantageously used for the implementation of an actuator digital control scheme generally known as impedance control. Other means to measure torque could include: measuring the torsion efforts on the flexspline 76 by means of strain gages; measuring the strain of some other transmission or structural elements by means of strain gages or other force or torque sensing devices.

Another benefit of the compliant transmission 34 is that the vibrations induced by the motor 52 and harmonic transmission assembly 56 are somewhat absorbed by the springs 156 and 158 instead of transmitted to the lower leg shank structure 12 and the components thereof. This helps to reduce the noise level generated by the prosthetic device 12.

Typical knee joint actuation mechanism 10 operation includes locomotion tasks commonly encountered in daily living. More specifically, level, upwards, and downwards surface walking, as well as stairs ascent, descent, standing-up, sitting-down, standing and sitting are the major locomotion tasks supported by the motorized prosthetic knee joint actuation mechanism 10. The knee joint actuation mechanism 10 design can be optimized for level walking task, accordingly, spring 156 and 158 stiffness is selected as the average knee joint stiffness during stance phase of the gait cycle, as found from non-amputee subject torque-position characteristics.

During level walking, presence of the mechanical springs 156 and 158 allows to passively (i.e., no motor movement is required, nor desirable) sustain stance phase knee flexion and optimize the energy exchange that takes place between the user and the motorized prosthetic knee actuation mechanism 10. Hence, following the occurrence of heel strike, a constant position command is sent to the motor 52, blocking the latter, and allowing the spring stack assembly 132 to extend as knee flexion occurs. Stored, energy then brings back the shank structure 12 in extension as the torque imposed on the shank structure reduces. Subsequent transition from late stance to early swing is also facilitated by the presence of the passive springs 156 and 158, which allows to gracefully transition the motor 52 behavior from constant position regulation to swing initiation trajectory.

In swing phase, the mechanism 10 adopts a force following behavior where the motor 52 is used to compensate inertial and friction efforts and restore natural dynamics, by using the spring-generated torque measurement as actuation command, following the completion of the initial push-off phase.

In ascent and descent locomotion portions, presence of the passive springs 156 and 158 both allow to ease foot placement and loading phases, as well as support the implementation of the force following swing phase, hence generating a system behavior-very similar to what can be observed on a normal joint. For power generation tasks, such as stairs ascent, inclined ascent or rising from a seated position, spring 156 and 158 non-linearity and deflection limitations are used, in order to control the impacts of the compliant-transmission elements on the torque and angular velocity capabilities of mechanism 10.

The deflection of the compliant transmission 34 causes a relative rotational movement to the third shaft 66 which is measured by the sensor assembly 112 (specifically the sensor partial disk 120 and its sensor detector 128).

Generally, the stiffness of the compliant transmission mechanism is determined by the stiffness of the normal human knee joint during the stance phase. As the human leg stiffness increases with walking speed, it was desired that the compliant transmission has a non-linear stiffness behavior. At faster walking speed (thus larger torque value), the compliant transmission mechanism generally demonstrates stiffer behavior than at slower walking speeds (thus lower torque).

Compliant Transmission Geometry

Figure 16:
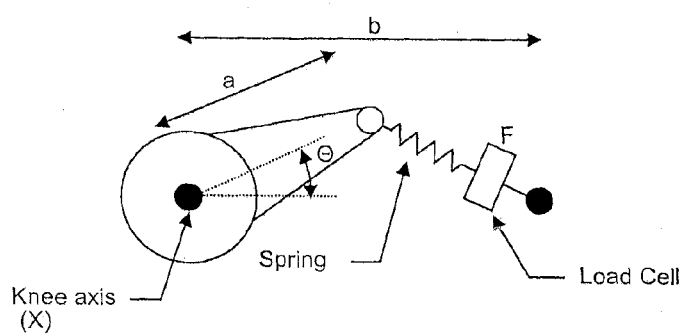
FIG. 16 is a schematic example representing the compliant transmission geometry of the invention in accordance with one non-limiting embodiment thereof.

In accordance with another embodiment of the invention and for more clarity, FIG. 16 shows a schematic representation of a compliant transmission geometry, with (a) representing the length of the knee lever such as 92; (b) representing the length of the transmission assembly such as 34; ($\Theta$) representing the angle of deflection measured on the knee rotating axis X; and F representing the force on the compliant member (depending on the stiffness of the springs 156 and 158 or on the load cell for example—as will be described for the orthotic mechanism 200).

Therefore, the geometry of an embodiment of the compliant transmission assembly of the present invention provides the required characteristics with a simple design. As explained, many considerations lead to the foregoing: the knee joint stiffness of the human leg while walking varies with cadence; the knee flexion amplitude varies with cadence; at higher torque levels, such as when going up the stairs, it is important to limit the magnitude of the deflection, in order to limit the energy stored in the system and increase equivalent stiffness at high torque levels; keeping a smooth transition between the "compliant" behavior and the flexion-limiting bumper.

Orthotic Device

With reference to FIGS. 17 to 20, a joint mechanism 200 is shown in accordance with another embodiment of the present invention. In this example the joint mechanism 200 is a knee-joint mechanism.

Figure 19:
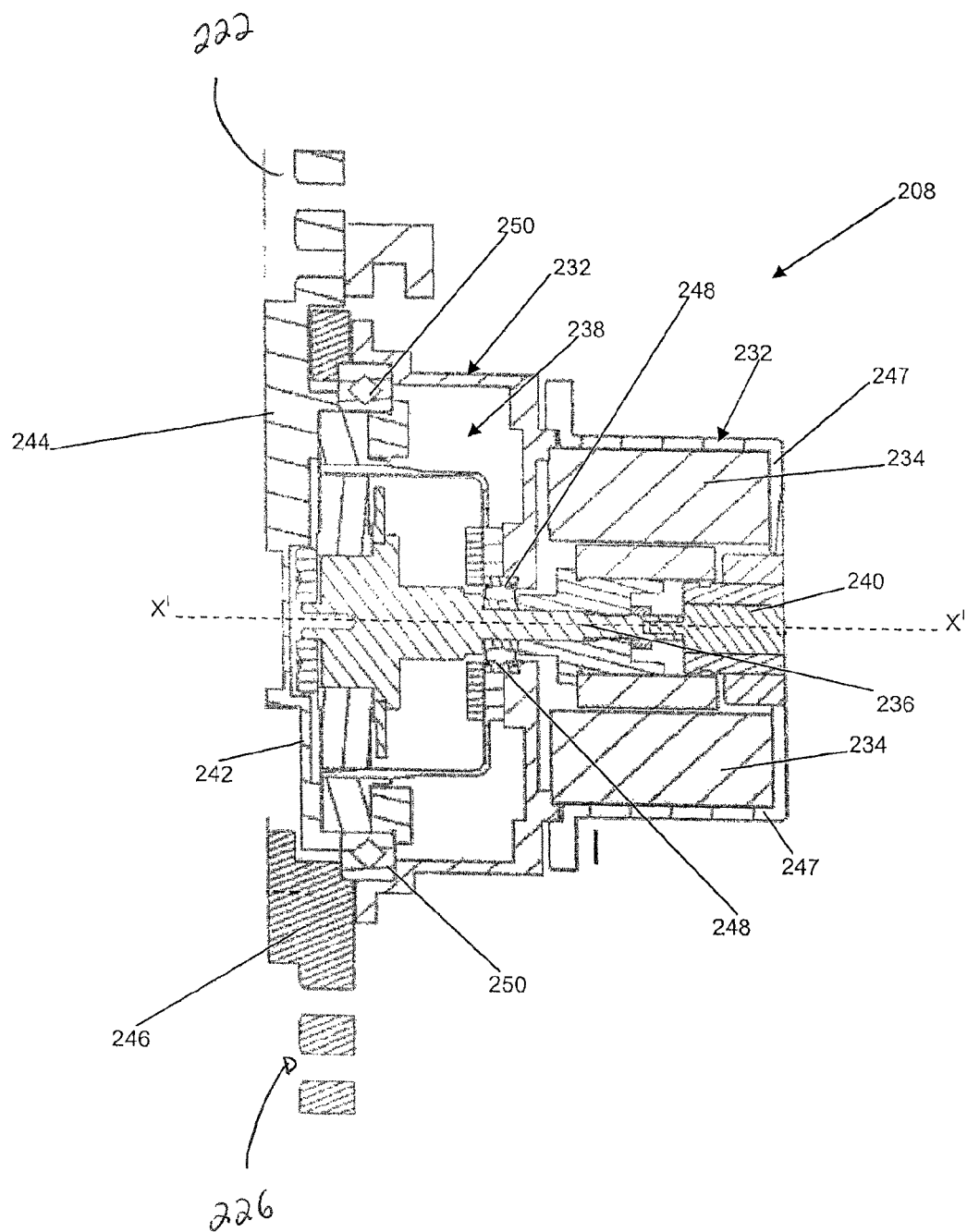
FIG. 19 is a schematic representation of an mechanical actuator assembly for the joint actuation mechanism of FIG. 17.

With particular reference to FIGS. 17 and 19, the knee joint mechanism 200 is mounted to and forms part of an orthotic leg support device 201 comprising a proximal orthotic portion or shell 202 for supporting a user's thigh segment 203, a distal orthotic portion or shell 204 for supporting a user's shank segment 205, with a knee support 206 therebetween for supporting the knee 207.

The knee support 206 comprises a lateral actuator mechanism 208 and medial hinge 210.

Battery packs 212 are integrated within the top element 214 of the proximal orthotic shell 202; whereas a processing platform 216 and power board 218 are integrated within a lower element 220 of the proximal orthotic shell 202.

In the present non-limiting example, the processing platform 216 comprises a CPU and I/O subsystem, hosting a knee actuator controller SW and the power board 218 comprises an actuator drive as well as a processing platform and battery power management circuitry.

The proximal orthotic shell 202 also comprises proximo-lateral structural support 222 connected to a torque-measurement load cell 224 which is connected to the lateral actuator mechanism 208. The distal orthotic shell 204 also comprises a distolateral structural supports 226 having a compliant transmission non-linear spring 228 mounted thereon and connected to a compliant transmission lever 230 on the lateral actuator mechanism 208. The distal orthotic shell 204 also includes a laterodistal sensor module 229 mounted on the lower element 231 of the shell 204.

Referring to FIG. 19, the lateral actuator mechanism 208 comprises a housing 232 for housing an actuator 234, such as a brushless motor for example, that is in operational communication with a shaft 236 that is in communication with a harmonic transmission assembly 238 at one end thereof and an actuator angular sensor 240 at another end thereof. The harmonic transmission cover 242 is connected to both a proximolateral anchor 244, which is mounted to the proximolateral structural support 222, and a distolateral anchor 246 (via the non-linear spring 228), which is mounted to the distolateral structural support 226. The brushless motor 234 is positioned within a stator 247 that is fixed to, the distolateral anchor 246.

The shaft 236 defines the axis of rotation X' of the orthotic knee mechanism 200. The shaft 236 is guided by bearings 248 during rotation thereof while the housing 232 is guided by bearings 250 during rotation about, the X' axis.

Figure 20:
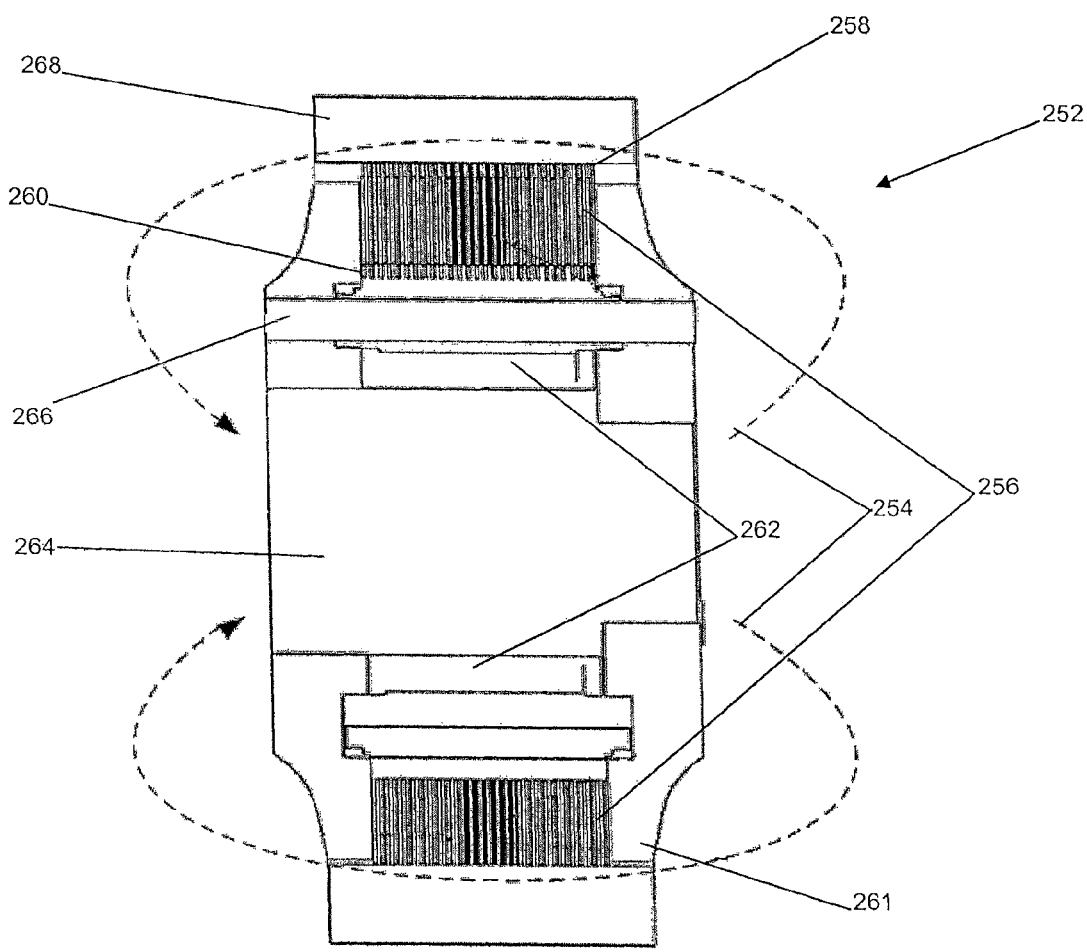
FIG. 20 is a schematic representation a Magnetorheological (MR) rotational damper for the joint actuation mechanism of FIG. 17.

In another embodiment shown in FIG. 20, instead of a mechanical actuator 228 a Magnetorheological (MR) rotational damper 252 is used. In the MR actuator 252, the dissipative braking torque is obtained by applying a magnetic field 254 through the magnetorheological fluid 256 occupying interstices between the stator blade array 258 and rotor blade array 260. Side plates 261 close the magnetic field 254 propagation path. Furthermore, the magnetic field 254 can be dynamically controlled by regulating the current circulating in the inductive coil 262 folded about the electromagnetic core 264. In the absence of a magnetic field 254, the magnetorheological fluid 256 viscosity is very low and the rotor body 266 is free to rotate inside the stator body 268. When the magnetic field 254 increases, the fluid's ferromagnetic particles align with the magnetic field 254 and created shear resistance between stator blades 258 and rotor blades 260, offering a breaking torque against applied moment through the knee joint.

Therefore, the orthotic knee actuation mechanism 200 comprises an actuator mechanism 208, a compliant transmission mechanism 300 (including lever 230 and spring 228) and a torque sensor 229.

In this way, the orthotic knee actuation mechanism 200 dynamically regulates the support provided to the user's knee 207. This dynamic regulation and compliant transmission avoids abrupt transitions between the locked and unlocked states of the knee hinge 210 during typical walking and descending locomotion tasks for example. In typical walking, the knee actuation mechanism 200 provides the ability to support the stance phase while allowing knee flexion for a more natural weight acceptance, from heel strike, to midstance. More over, the knee actuation mechanism 200 significantly improves transitions between stance and swing phases, where the knee actuator 208 can provide appropriate support without abrupt locking and unlocking events. For descending portions, the ability of both actuator 208 implementations to absorb potential energy through passive damping during knee flexion provides step over step ambulation.

In essence, the compliant element of the invention absorbs energy during flexion of a joint for the dampening thereof and releases this energy during extension of the joint for assistance thereof. In an embodiment, the compliant element of the invention stores energy during flexion of a joint for the retardation thereof and releases this energy during extension of the joint for the acceleration thereof.

Compliant Transmission Assembly

With respect to FIGS. 21A, 21B, 21C, 21D and 21E, show a variety of general schematic alternative embodiments of the compliant transmission of the present invention.

Figure 21A:
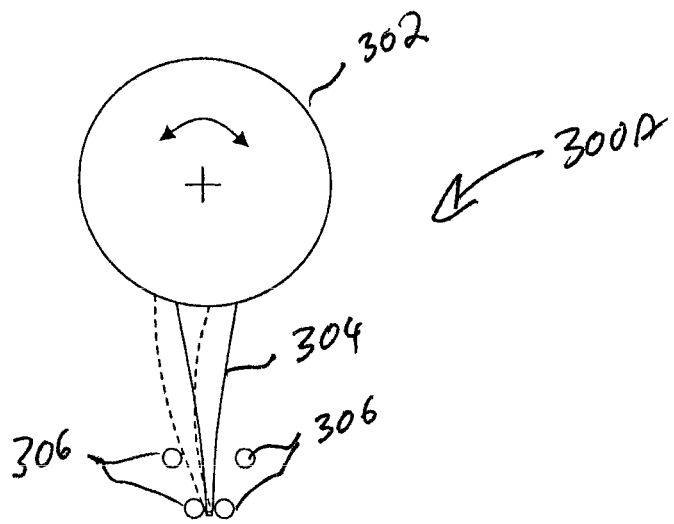
FIGS. 21A, 21B, 21C, 21D and 21E, are schematic representation of a variety compliant transmission assemblies in accordance with non-limiting embodiments of the present invention.
Figure 21B:
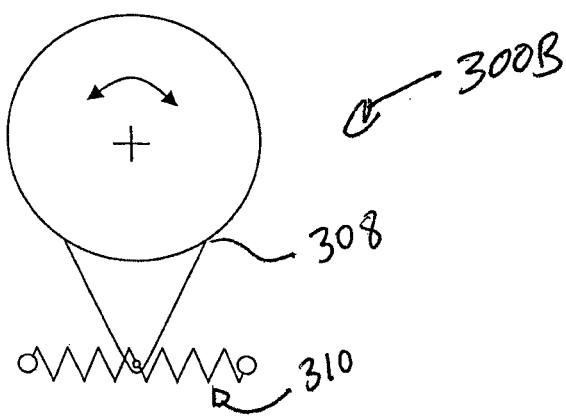
Figure 21C:
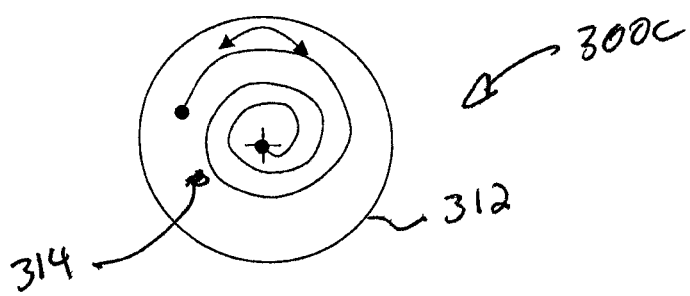
Figure 21D:
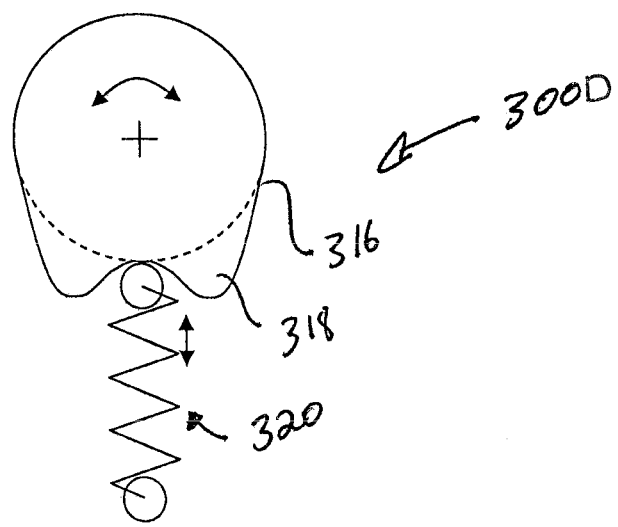
Figure 21E:
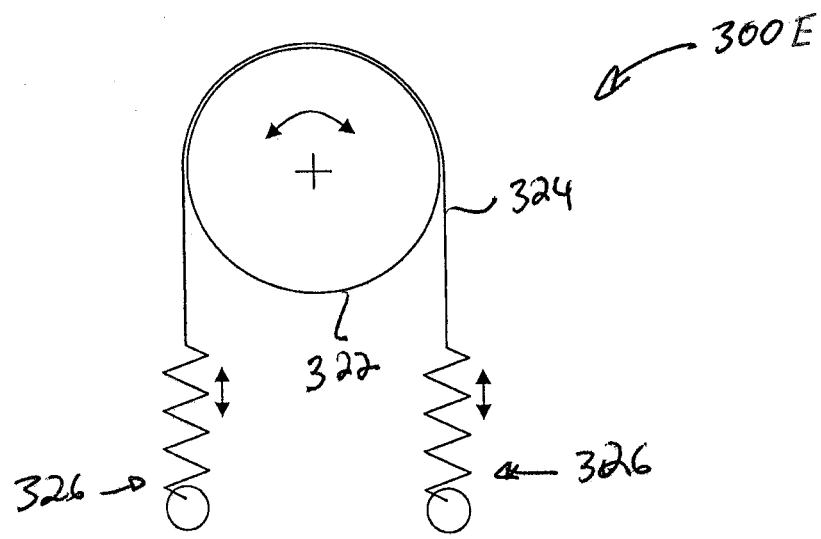

FIG. 21A represents a compliant transmission assembly 300A having a lever or cam 302 and a compliant element 304 which can be a cross-shaped or cylindrical shaft in torsion, a beam in flexion, that can be guided by mechanical stops 306. Many mechanical stops can be used to provide non-linear stiffness as is required. FIG. 21B shows a compliant transmission assembly 300B having a lever or cam 308 and a linear compliant element 310 which can be made of a variety of flexible structural components. In one embodiment, the linear compliant element 310 comprises linear springs such as Belville washers, helical springs, elastomer springs, gas springs and the like. FIG. 21C shows a compliant transmission assembly 300C having a lever or cam 312 and a compliant element 314 in the form of a constant force spring. FIG. 21D shows a compliant transmission 300D having a lever or cam 316, a cam follower 318 loaded with a compliant element 320 such as springs. FIG. 21E shows a compliant transmission 300E having a lever or cam 322, a belt 324 mounted to compliant elements 326 such as springs.

Torque can be evaluated by measuring the deflection of the compliant transmission. Other means for measuring the torque could include the following non-limiting implementations:

strain gages on the flexible cup of the compliant transmission;

load cell or strain gages on structural components to measure torque;

load cell in series with the elastic element to directly measure the force applied on the elastic element;

Strain gages placed directly on the elastic element; and the load cells could utilize strain gages, piezo-ceramic force transducer or any other appropriate technology.

In the non-limiting examples discussed herein, the joint actuation mechanism is a knee actuation mechanism, of course a similar mechanism can also be used for an elbow joint or other joints of the human body for either prosthetic or orthotic devices. These mechanisms can be powered or not.

The skilled artisan can contemplate a variety of compliant transmission structures for joint actuation mechanism for orthotic or prosthetic devices within the context of the present invention. As such, a variety of compliant elements, such as springs and the like can be used with various compliant element carrying bodies. These compliant elements can operationally communicate with the prosthetic or orthotic joint mechanism via various structural connections as a skilled artisan can contemplate and design within the scope of the present invention.

The skilled artisan will readily understand that the various features of the various embodiments discussed herein can be combined in a variety of ways so as to produce other non-illustrated examples within the context of the present invention.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of embodiments thereof, it can be modified, without departing from the spirit, scope and nature of the subject invention.

What is claimed is:

1. A prosthetic knee device comprising:
a knee joint interposed between a prosthetic shin and another adjacent prosthetic portion or an adjacent limb segment of a user, said knee joint comprising a joint actuator assembly for providing said prosthetic shin to pivot between flexion and extension movements relative to said another adjacent prosthetic portion or the adjacent limb segment of the user when mounted thereto;
a compliant transmission assembly in operational communication with said knee joint via a rotatable connector mounted to a compliant member and said knee joint, the rotatable connector located between the joint actuator assembly and the compliant transmission assembly, wherein said compliant member absorbs energy and rotates relative to the prosthetic shin when a torque is applied between said prosthetic shin and said another adjacent prosthetic portion or the adjacent limb segment of the user;

a sensor that provides for torque measurement; and a controller configured to use said torque measurement to control said joint actuator assembly;

wherein during a stance phase of the gait cycle the prosthetic knee device is configured so that the actuator assembly does not provide said pivot between flexion and extension and the compliant transmission assembly absorbs and returns energy; and wherein during a swing phase of the gait cycle the prosthetic knee device is configured so that the controller causes the actuator assembly to adopt a force following behavior based on the torque measurement.

2. A prosthetic knee device according to claim 1, wherein said compliant member absorbs energy during flexion and releases this energy during extension.

3. A prosthetic knee device according to claim 1, wherein when absorbing energy said compliant member dampens flexion of said prosthetic knee device and when releasing energy said compliant member assists extension of said prosthetic knee device.

4. A prosthetic knee device according to claim 1, wherein said compliant member comprises at least one compliant element, said compliant element being a deformable and resilient element.

5. A prosthetic knee device according to claim 4, wherein said compliant member comprises a pair of side by side compliant elements.

6. A prosthetic knee device according to claim 5, wherein said compliant elements are springs.

7. A prosthetic knee device according to claim 5, wherein said compliant elements are placed under stress by a stress member.

8. A prosthetic knee device according to claim 7, wherein said stress member comprises a pair of stress tubes having a bottom platform and a top shoulder for sandwiching therebetween said compliant elements.

9. A prosthetic knee device according to claim 8, wherein each said stress tube includes a respective stress actuator for providing a predetermined pre-stress to each compliant element.

10. A prosthetic knee device according to claim 1, wherein said rotatable connector comprises a lever.

11. A prosthetic knee device according to claim 1, wherein said rotatable connector is integrally mounted to said knee joint.

12. A prosthetic knee device according to claim 1, wherein said rotatable connector is mounted to said compliant member via a pivot.

13. A prosthetic knee device according to claim 12, wherein flexion and extension movements cause a respective deflection between said rotatable connector and said compliant member about said pivot.

14. A prosthetic knee device according to claim 1, wherein said compliant transmission assembly further comprises a pivot interposed between said compliant member and said knee joint.

15. A prosthetic knee device according to claim 14, wherein flexion and extension movements cause a respective deflection between said knee joint and said compliant member about said pivot.

16. A prosthetic knee device according to claim 15, wherein the sensor senses said deflection.

17. A prosthetic knee device according to claim 16, wherein said sensor is mounted to said joint actuator assembly.

18. A prosthetic knee device according to claim 17, wherein said sensor is mounted to said compliant transmission assembly.

19. A prosthetic knee device according to claim 1, wherein said prosthetic shin comprises a proximal end and an opposite distal end, said opposite distal end provides for receiving a prosthetic foot member.

20. A prosthetic knee device according to claim 1, further comprising at least one additional joint.

21. A prosthetic knee device according to claim 1, wherein said another adjacent prosthetic portion comprises a proximal end and an opposite distal end, said proximal end comprising a socket for being mounted to the adjacent limb segment of the user.

22. A prosthetic knee device according to claim 1, wherein said compliant member is a non-linear compliant member providing the prosthetic knee device with a normal torque stiffness.

23. The prosthetic knee device of claim 1, further comprising a rotational axis sensor.

24. The prosthetic knee device of claim 23, wherein the rotational axis sensor is an optical sensor.

25. The prosthetic knee device of claim 24, wherein the optical sensor comprises a partial disk, light emitter, and sensor element.

26. The prosthetic knee device of claim 1, further comprising an actuator locking device for manually locking the knee joint at a desired knee angle.

27. The prosthetic knee device of claim 26, wherein the desired angle is at a 90 degree rotation.

28. The prosthetic knee device of claim 26, wherein the actuator locking device comprises a locking slider and a locking slider guide.

29. The prosthetic knee device of claim 28, wherein the actuator locking device further comprises a frictional brake.

30. The prosthetic knee device of claim 26, wherein the actuator locking device is configured to lock the knee joint at multiple angles.

31. The prosthetic knee device according to claim 1, wherein said connector is disengageable from said compliant member.

32. The prosthetic knee device of claim 1, wherein the sensor provides for torque measurement based on a deflection of the compliant member.

33. The prosthetic knee device of claim 1, wherein the sensor provides for torque measurement based on a rotation of the compliant transmission assembly relative to the prosthetic shin.

34. The prosthetic knee device of claim 1, wherein the sensor provides for torque measurement by means of a strain gage.

35. A prosthetic knee device comprising:
a knee-joint assembly comprising a prosthetic connector configured to connect the knee joint assembly to a user, a shaft, an inward-facing spline, and a first actuator portion;
a harmonic transmission assembly rotatably mounted on said shaft, the harmonic drive assembly comprising:
a second actuator portion configured to interact with the first actuator portion to provide a rotational motion;
a wave generator rotationally fixed to said second actuator portion, the wave generator comprising a transmission portion forming a generally elliptical surface at its periphery comprising a longest axis defining two contact portions; and a flexible cup comprising a flexspline, said flexspline comprising an inner surface mounted on the elliptical surface of the wave generator at the two contact portions, and an outer spline surface configured to engage with the inward-facing spline of the knee-joint assembly at locations corresponding to the two contact portions, wherein rotation of the wave generator causes the flexspline to flex such that the locations of engagement between the flexspline and the inward-facing spline rotates with the wave generator, and wherein the inward-facing spline and the flexspline have a different number of spline teeth;

a lever fixed to the flexible cup;

a spring assembly rotatably mounted to the lever via a moving pivot located between the spring assembly and the flexible cup, wherein the spring assembly exhibits a non-linear stiffness behavior configured to correspond with a normal human knee joint; and a shank rotatably mounted relative to the flexible cup and separately rotatably mounted to the spring assembly, such that rotation of the shank relative to the flexible cup is resisted by the spring assembly.

36. A prosthetic knee device comprising:

a prosthetic connector configured to be connected to a leg socket;

a knee joint actuator assembly comprising an actuator housing connected to the prosthetic connector and housing an actuator comprising a motor;

a rotatable shin structure configured to rotate about a pivot axis relative to the actuator housing, said rotation configured to be powered by the actuator to cause flexion and extension movements, wherein the actuator is mounted about the pivot axis;

a compliant transmission assembly connected between the rotatable shin structure and the knee joint actuator assembly, said compliant transmission assembly comprising a connector mounted to a compliant member and the knee joint actuator assembly, the compliant member being also mounted to the rotatable shin structure, a sensor that provides for torque measurement based on deflection of the compliant member; and a controller configured to use the torque measurement to control the actuator;

wherein during a stance phase of a gait cycle the prosthetic knee device is configured so that:

said compliant member first absorbs energy from ground contact and deflects relative to the rotatable shin structure, and then releases energy and moves back toward an undeflected position, and said motor of said actuator is immobilized; and wherein during a swing phase of the gait cycle the prosthetic knee device is configured so that the controller causes the actuator to adopt a force following behavior, based on the torque measurement, in cooperation with energy released or absorbed by the compliant member.

37. The prosthetic knee device of claim 36, wherein the knee joint actuator assembly further comprises a harmonic drive assembly.

38. The prosthetic knee device of claim 36, wherein the connector is rotatably mounted to the compliant member.

39. The prosthetic knee device of claim 36, wherein the compliant member is rotatably mounted to the rotatable shin structure.

40. The prosthetic knee device of claim 36, wherein the compliant member deflects forward during a stance phase of a gait cycle as the compliant member absorbs energy.

41. The prosthetic knee device of claim 36, wherein the compliant member deflects backward during a stance phase of a gait cycle as the compliant member releases energy.

42. The prosthetic knee device of claim 36, wherein the rotatable shin structure has a flexion movement during a stance phase of a gait cycle as the compliant member absorbs energy.

43. The prosthetic knee device of claim 36, wherein the rotatable shin structure has an extension movement during a stance phase of a gait cycle as the compliant member releases energy.

* * * * *

UNITED STATES PATENT AND TRADEMARK OFFICE
CERTIFICATE OF CORRECTION

| | |
|---|---|
| PATENT NO. | : 8,435,309 B2 |
| APPLICATION NO. | : 12/160727 |
| DATED | : May 7, 2013 |
| INVENTOR(S) | : Gilbert et al. |

It is certified that error appears in the above-identified patent and that said Letters Patent is hereby corrected as shown below:

In the Specification

In column 2 at line 4, Change "invention" to --invention,--.

In column 2 at line 12, Change "thereof" to --thereof,--.

In column 2 at line 37, Change "tan" to --an--.

In column 2 at line 47, Change "a A" to --a--.

In column 2 at line 52, Change "flexion, and," to --flexion and--.

In column 3 at line 46, Change "mechanism" to --mechanism,--.

In column 4 at line 38, Change "impossible" to --possible--.

In column 6 at line 30, Change "face's" to --faces--.

In column 6 at line 33, Change "shin," to --shin--.

In column 6 at line 41, Change "shank," to --shank--.

In column 6 at line 46, Change "connector" to --connector 32--.

In column 6 at line 47, Change "ankle," to --ankle--.

In column 7 at line 22, Change "flexspine" to --flexspline--.

In column 7 at line 32, Change "wail" to --wall--.

In column 7 at line 35, Change "ouster" to --outer--.

In column 7 at line 61, Change "type." to --type--.

In column 7 at line 65, Change "output," to --output--.

In column 8 at line 59, Change "rotating" to --rotating,--.

In column 8 at line 59, Change "and," to --and--.

In column 8 at line 61, Change "transmission," to --transmission--.

In column 8 at line 63, Change "element," to --element--.

In column 8 at line 65, Change "tends," to --tends--.

Signed and Sealed this
Eighth Day of October, 2013

Teresa Stanek Rea
*Deputy Director of the United States Patent and Trademark Office*

In column 9 at line 14, Change "334" to --34--.

In column 9 at line 33, Change "flexible," to --flexible--.

In column 9 at line 44, Change "118'" to --118--.

In column 9 at line 45, Change "element," to --element--.

In column 9 at line 53, Change "is" to --as--.

In column 9 at line 59, Change "connecting," to --connecting--.

In column 11 at line 24, Change "braking," to --braking--.

In column 11 at line 44, Change "thus," to --thus--.

In column 11 at line 44, Change "sensor of" to --sensor--.

In column 12 at line 10, Change "flesxpsline" to --flexspline--.

In column 12 at line 31, Change "force," to --force--.

In column 12 at line 38, Change "fore" to --for--.

In column 12 at line 42, Change "±1.5" to --±15--.

In column 12 at line 54, Change "(1.5" to --(15--.

In column 12 at line 63, Change "off" to --of--.

In column 12 at line 67, Change "122," to --122--.

In column 13 at line 23, Change "task," to --task;--.

In column 13 at line 35, Change "Stored," to --Stored--.

In column 13 at line 42, Change "force" to --force- --.

In column 13 at line 51, Change "-very" to --very--.

In column 13 at line 54, Change "used," to --used--.

In column 13 at line 55, Change "compliant-" to --compliant--.

In column 14 at line 29, Change "knee-" to --knee--.

In column 14 at line 53, Change "supports" to --support--.

In column 15 at line 3, Change "to," to --to--.

In column 15 at line 8, Change "about," to --about--.

In column 15 at line 39, Change "strike," to --strike--.

In column 15 at line 40, Change "More over," to --Moreover,--.

In the Claims

In column 16 at line 31, change "such," to --such--.

UNITED STATES PATENT AND TRADEMARK OFFICE
CERTIFICATE OF CORRECTION

| | | |
|---|---|---|
| PATENT NO. | : 8,435,309 B2 | Page 1 of 1 |
| APPLICATION NO. | : 12/160727 | |
| DATED | : May 7, 2013 | |
| INVENTOR(S) | : Benoit Gilbert et al. | |

It is certified that error appears in the above-identified patent and that said Letters Patent is hereby corrected as shown below:

On the title page, item (60), please delete "60/878,689" and insert --60/878,690-- therefor Signed and Sealed this
Twelfth Day of July, 2016

Michelle K. Lee
*Director of the United States Patent and Trademark Office*